(12) United States Patent
Phadke et al.

(10) Patent No.: US 9,085,607 B2
(45) Date of Patent: Jul. 21, 2015

(54) ACH-0142684 SODIUM SALT POLYMORPH, COMPOSITION INCLUDING THE SAME, AND METHOD OF MANUFACTURE THEREOF

(71) Applicant: Achillion Pharmaceuticals Inc., New Haven, CT (US)

(72) Inventors: Avinash Phadke, Branford, CT (US); Akihiro Hashimoto, Branford, CT (US); Pingyun Chen, Chapel Hill, NC (US); Senthil Kumar Kusalakumari Sukumar, Raleigh, NC (US)

(73) Assignee: ACHILLION PHARMACEUTICALS, INC., New Haven, CT (US)

( * ) Notice: Subject to any disclaimer, the term of this patent is extended or adjusted under 35 U.S.C. 154(b) by 0 days.

(21) Appl. No.: 14/216,072

(22) Filed: Mar. 17, 2014

(65) Prior Publication Data

US 2014/0274914 A1    Sep. 18, 2014

Related U.S. Application Data

(60) Provisional application No. 61/788,198, filed on Mar. 15, 2013.

(51) Int. Cl.
  *C07K 5/12* (2006.01)
  *C07K 5/083* (2006.01)
  *C07D 417/14* (2006.01)

(52) U.S. Cl.
  CPC ............ *C07K 5/0808* (2013.01); *C07D 417/14* (2013.01); *C07B 2200/13* (2013.01)

(58) Field of Classification Search
  None
  See application file for complete search history.

(56) References Cited

U.S. PATENT DOCUMENTS

| | | | |
|---|---|---|---|
| 6,867,185 B2 | 3/2005 | Campbell et al. | |
| 6,872,805 B2 | 3/2005 | Campbell et al. | |
| 6,908,901 B2 | 6/2005 | Bailey et al. | |
| 6,995,174 B2 | 2/2006 | Wang et al. | |
| 7,041,698 B2 | 5/2006 | Ripka et al. | |
| 7,176,208 B2 | 2/2007 | Nakajima et al. | |
| 7,659,263 B2 | 2/2010 | Mizojiri et al. | |
| 7,906,619 B2 | 3/2011 | Phadke et al. | |
| 2002/0198378 A1 | 12/2002 | Vazquez et al. | |
| 2003/0224977 A1 | 12/2003 | Llinas-Brunet et al. | |
| 2004/0002448 A1 | 1/2004 | Tsantrizos et al. | |
| 2004/0048802 A1 | 3/2004 | Ripka et al. | |
| 2004/0077551 A1 | 4/2004 | Campbell et al. | |
| 2004/0106559 A1 | 6/2004 | Wang et al. | |
| 2004/0180815 A1 | 9/2004 | Nakajima et al. | |
| 2004/0224900 A1 | 11/2004 | Bailey et al. | |
| 2005/0020503 A1 | 1/2005 | Llinas-Brunet et al. | |
| 2005/0153877 A1 | 7/2005 | Miao et al. | |
| 2005/0267040 A1 | 12/2005 | Scola et al. | |
| 2006/0019905 A1 | 1/2006 | Bailey et al. | |
| 2006/0046965 A1 | 3/2006 | Bailey et al. | |
| 2006/0046983 A1 | 3/2006 | Hudyma et al. | |
| 2006/0142204 A1 | 6/2006 | Halfon et al. | |
| 2006/0199773 A1 | 9/2006 | Sausker et al. | |
| 2006/0281688 A1 | 12/2006 | Zhang et al. | |
| 2007/0010455 A1 | 1/2007 | Hewawasam et al. | |
| 2007/0093414 A1 | 4/2007 | Carini et al. | |
| 2007/0099825 A1 | 5/2007 | D'Andrea et al. | |
| 2009/0048297 A1 | 2/2009 | Phadke et al. | |
| 2010/0216725 A1 | 8/2010 | Phadke et al. | |

FOREIGN PATENT DOCUMENTS

| | | |
|---|---|---|
| JP | 2002542160 A | 10/2002 |
| JP | 2007524576 A | 8/2007 |
| WO | 9101327 A1 | 2/1991 |
| WO | 9325574 A1 | 12/1993 |
| WO | 0059929 A1 | 10/2000 |
| WO | 02060926 A2 | 8/2002 |
| WO | 03099274 A1 | 12/2003 |
| WO | 03099316 A1 | 12/2003 |
| WO | 2004043339 A2 | 5/2004 |
| WO | 2004072243 A1 | 8/2004 |
| WO | 2004094452 A2 | 11/2004 |
| WO | 2004103996 A1 | 12/2004 |
| WO | 2004113365 A2 | 12/2004 |
| WO | 2005028501 A1 | 3/2005 |
| WO | 2005037214 A2 | 4/2005 |
| WO | 2005046712 A2 | 5/2005 |
| WO | 2005051410 A1 | 6/2005 |
| WO | 2005054430 A2 | 6/2005 |
| WO | 2005070955 A1 | 8/2005 |
| WO | 2005073216 A1 | 8/2005 |

(Continued)

OTHER PUBLICATIONS

Andrews, et al., "Pyrrolidine-5,5-trans-lactams. 2. The Use of X-ray Crystal Structure Data in the Optimization of P3 and P4 Substituents," Organic Letters, 4(25): 4479-4482 (2002).

Arasappan, et al., "Hepatitis C Virus N53-4A serine protease inhibitors: SAR of P2 moiety with improved potency," Bioorganic & Medicinal Chemistry Letters, 15: 4180-4184 (2005).

Barbato, et al., "Inhibitor binding induces active site stabilization of the HCV NS3 protein serine protease domain," The EMBO Journal, 19(6): 1195-1206 (2000).

Di Marco, et al., "Inhibition of the Hepatitis C Virus NS3/4A Protease," The Journal of Biological Chemistry, 275(10): 7152-7157(2000).

Liu, et al., "Hepatitis C NS3 protease inhibition by peptidyl-alpha-ketoamide inhibitors: kinetic mechanism and structure," Biochemistry and Biophysics, 421: 207-216 (2004).

(Continued)

*Primary Examiner* — Christina Bradley
(74) *Attorney, Agent, or Firm* — Cantor Colburn LLP

(57) ABSTRACT

The disclosure provides a crystalline sodium salt of ACH-0142684 comprising a Form A polymorph, a Form B polymorph, a Form C polymorph, a Form D polymorph, a Form E polymorph, a Form F polymorph, a Form G polymorph, a Form H polymorph, a Form I polymorph, or a combination thereof, wherein the Form A, B, C, D, E, F, G, H, and I polymorph exhibits an X-ray powder diffraction pattern having peak locations in accordance with FIGS. 8; 12; 15; 21; 22; 27; 30, and 31, respectively.

20 Claims, 33 Drawing Sheets

(56) References Cited

FOREIGN PATENT DOCUMENTS

| | | | |
|---|---|---|---|
| WO | 2005090383 A2 | | 9/2005 |
| WO | 2005095403 A2 | | 10/2005 |
| WO | 2006007700 A1 | | 1/2006 |
| WO | 2006007708 A1 | | 1/2006 |
| WO | 2006020276 A2 | | 2/2006 |
| WO | 2006033878 A1 | | 3/2006 |
| WO | 2006086381 A2 | | 8/2006 |
| WO | 2006096652 A2 | | 9/2006 |
| WO | 2005007681 A2 | | 1/2007 |
| WO | 2007005838 A2 | | 1/2007 |
| WO | 2007009109 A2 | | 1/2007 |
| WO | 2007009227 A1 | | 1/2007 |
| WO | 2007014919 A1 | | 2/2007 |
| WO | 2007014927 A3 | | 2/2007 |
| WO | 2007015824 A2 | | 2/2007 |
| WO | 2007030656 A1 | | 3/2007 |
| WO | 2007044893 A2 | | 4/2007 |
| WO | 2008008502 A1 | | 1/2008 |
| WO | 2008086161 A1 | | 7/2008 |
| WO | WO 2010/068761 | * | 6/2010 |

OTHER PUBLICATIONS

Llinas Brunet, et al., "A Systematic Approach to the Optimization of Substrate-Based Inhibitors of the Hepatitis C Virus NS3 Protease: Discovery of Potent and Specific Tipeptide Inhibitors," J. Med. Chem., 47: 6584-6594.

Rakic, et al., "A Small-Molecule Probe for Hepatitis C Virus Replication that Blocks Protein Folding," Chemistry & Biology, 13: 1051-1060 (2006).

Slater, et al., "Pyrrolidine-5,5-trans-lactams. 4. Incorporation of a P3/P4 Urea Leads to Potent Intracellular Inhibitors of Hepatitis C Virus NS3/4A Protease," Organic Letters, 5(24): 4627-4630 (2003).

Tsantrizos, et al., "Macrocyclic Inhibitors of the NS3 Protease as Potential Therapeutic Agents of Hepatitis C Virus Infection," Agnew. Chem. Int. Ed., 42(12): 1355-1360 (2003).

Venkatraman, et al., "Discovery of (1R,5S)-N-[3-Amino-1-(cyclobutylmethyl)-2,3-dioxopropyl]-3-[2(S)-[[[(1,1-dimethyl-lethyl)amino]carbonyl] amino]-3,3-dimethyl-1-oxobutyl]-6,6-dimethyl-3-azabicyclo[3.1.0]hexan-2(S)-carboxamide (SCH 503034), a Selective, Potent, Orally Bioavailable Hepatitis C Virus NS3 Protease Inhibitor: A Potential Therapeutic Agent for the Treatment of Hepatitis C Infection", J. Med. Chem. 2006, 6074-6086.

* cited by examiner

ACH-0142684 SODIUM SALT POLYMORPH, COMPOSITION INCLUDING THE SAME, AND METHOD OF MANUFACTURE THEREOF

CROSS REFERENCE TO RELATED APPLICATION

This application claims priority from U.S. Provisional application No. 61/788,198 filed Mar. 15, 2013, which is hereby incorporated by reference in its entirety.

FIELD OF THE DISCLOSURE

Disclosed are ACH-0142684 sodium salt polymorphs, pharmaceutical compositions and preparations containing the ACH-0142684 sodium salt polymorphs, and methods of manufacture thereof.

BACKGROUND

The molecules in a crystalline solid are arranged in a crystal lattice, a three dimensional structure in which structural units (unit cells) are repeated in a regular manner. Different crystal forms of the same substance (polymorphs) have distinct crystal lattices, which can result in important differences in their properties, utilities, and commercial values. For example, graphite and diamond are polymorphs of crystalline carbon. Polymorphs of pharmaceutical compounds can also be distinctly, if not as dramatically, different in their properties, including properties relevant to the development of formulations of such pharmaceutical compounds and to the development of solid dosage forms, such as tablets and capsules, comprising such formulations. The crystal form of a drug may also be relevant to compliance with regulatory requirements concerning its manufacture.

ACH-0142684 sodium salt has been identified as useful for the treatment of chronic HCV infection. To improve therapeutic use of ACH-0142684 sodium salt, identification of new polymorphs of ACH-0142684 sodium salt would be desirable.

SUMMARY

Disclosed herein is a crystalline sodium salt of ACH-0142684 comprising a Form A polymorph, a Form B polymorph, a Form C polymorph, a Form D polymorph, a Form E polymorph, a Form F polymorph, a Form G polymorph, a Form H polymorph, a Form I polymorph, or a combination thereof, wherein the Form A polymorph exhibits an X-ray powder diffraction pattern having peak locations in accordance with FIG. 8, the Form B polymorph exhibits an X-ray powder diffraction pattern having peak locations in accordance with FIG. 12, the Form C polymorph exhibits an X-ray powder diffraction pattern having peak locations in accordance with FIG. 15, the Form D polymorph exhibits an X-ray powder diffraction pattern having peak locations in accordance with FIG. 18, the Form E polymorph exhibits an X-ray powder diffraction pattern having peak locations in accordance with FIG. 21, the Form F polymorph exhibits an X-ray powder diffraction pattern having peak locations in accordance with FIG. 24, the Form G polymorph exhibits an X-ray powder diffraction pattern having peak locations in accordance with FIG. 27, the Form H polymorph exhibits an X-ray powder diffraction pattern having peak locations in accordance with FIG. 30, the Form I polymorph exhibits an X-ray powder diffraction pattern having peak locations in accordance with FIG. 31, or a combination thereof.

Also disclosed herein is a composition comprising a crystalline sodium salt of ACH-0142684 and a pharmaceutically acceptable carrier, wherein at least 90% of the crystalline sodium salt of ACH-0142684 is the Form A polymorph, the Form B polymorph, the Form C polymorph, the Form D polymorph, the Form E polymorph, the Form F polymorph, the Form G polymorph, the Form H polymorph, the Form I polymorph, or a combination thereof.

Also disclosed herein is a pharmaceutical composition comprising the crystalline sodium salt of ACH-0142684 as disclosed above, in combination with a physiologically acceptable carrier or excipient.

Also disclosed herein is a method for treating HCV, comprising administering to a patient in need of such treatment a therapeutically effective amount of a pharmaceutical composition as disclosed above.

The above described and other features are exemplified by the following figures and detailed description.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
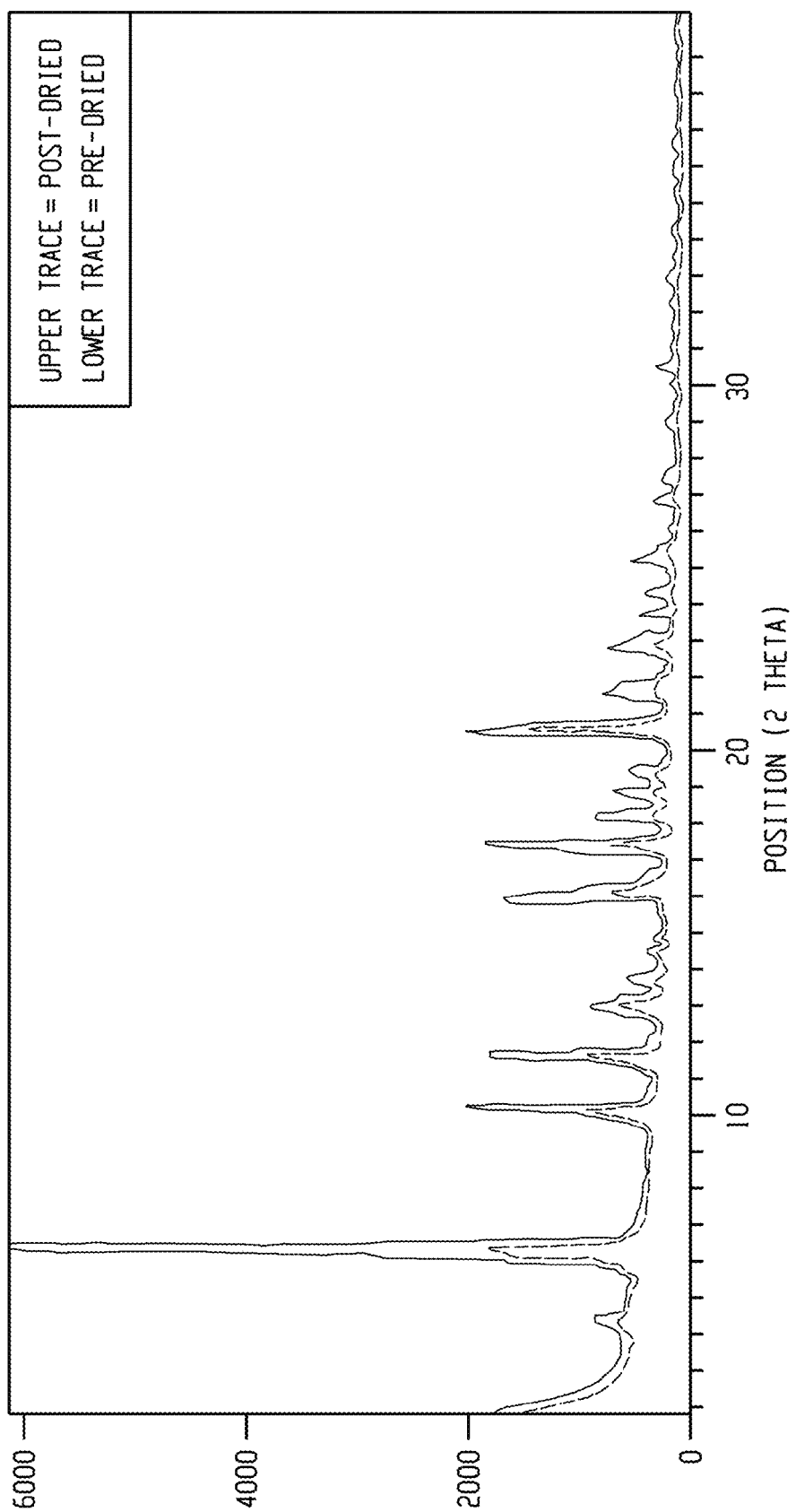
FIG. 1 is a graph of intensity (counts per second) versus scattering angle (degrees 2θ) showing the results of X-ray powder diffraction analysis of pre-dried (lower trace) and post-dried (upper trace) Polymorph A sample.

The disclosure now will be described more detail, with reference to the accompanying figures. This disclosure may, however, be embodied in many different forms, and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

Terminology

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, i.e., the sodium salt of ACH-0142684, and at least one other substance, such as a carrier, excipient, or diluent. Pharmaceutical compositions meet the U.S. FDA's GMP (good manufacturing practice) standards for human or non-human drugs.

The term "carrier" applied to pharmaceutical compositions described herein refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing the sodium salt of ACH-0142684 with at least one additional active agent" means the sodium salt of ACH-0142684 and the additional active agent(s) are provided simultaneously in a single dosage form, provided concomitantly in separate dosage forms, or provided in separate dosage forms for administration separated by some amount of time that is within the time in which both the sodium salt of ACH-0142684 and the at least one additional active agent are within the blood stream of a patient. The sodium salt of ACH-0142684 and the additional active agent need not be prescribed for a patient by the same medical care worker. The additional active agent or agents need not require a prescription. Administration of the sodium salt of ACH-0142684 or the at least one additional active agent can occur via any appropriate route, for example, oral tablets, oral capsules, oral liquids, inhalation, injection, suppositories or topical contact.

"Treatment," as used herein includes providing sodium salt of ACH-0142684 and at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of the sodium salt of ACH-0142684 and at least one additional active agent to a patient having or susceptible to a hepatitis C infection.

A "therapeutically effective amount" of a pharmaceutical combination of this disclosure means an amount effective, when administered to a patient, to provide a therapeutic benefit such as an amelioration of symptoms, e.g., an amount effective to decrease the symptoms of a hepatitis C virus infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the limit of quantitation (30 IU/mL, as measured by the Roche TaqMan(R) assay) or more preferably below the limit of detection (10 IU/mL, Roche TaqMan).

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The sodium salt of ACH-0142684 has the following structure (1):

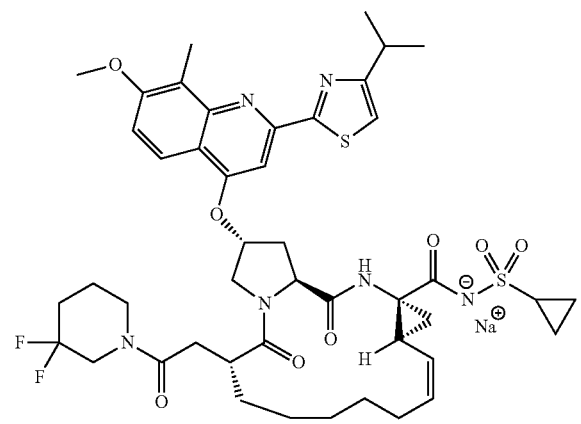

Disclosed herein is a crystalline sodium salt of ACH-0142684 comprising a Form A polymorph, a Form B polymorph, a Form C polymorph, a Form D polymorph, a Form E polymorph, a Form F polymorph, a Form G polymorph, a Form H polymorph, a Form I polymorph, or a combination thereof.

Figure 7:
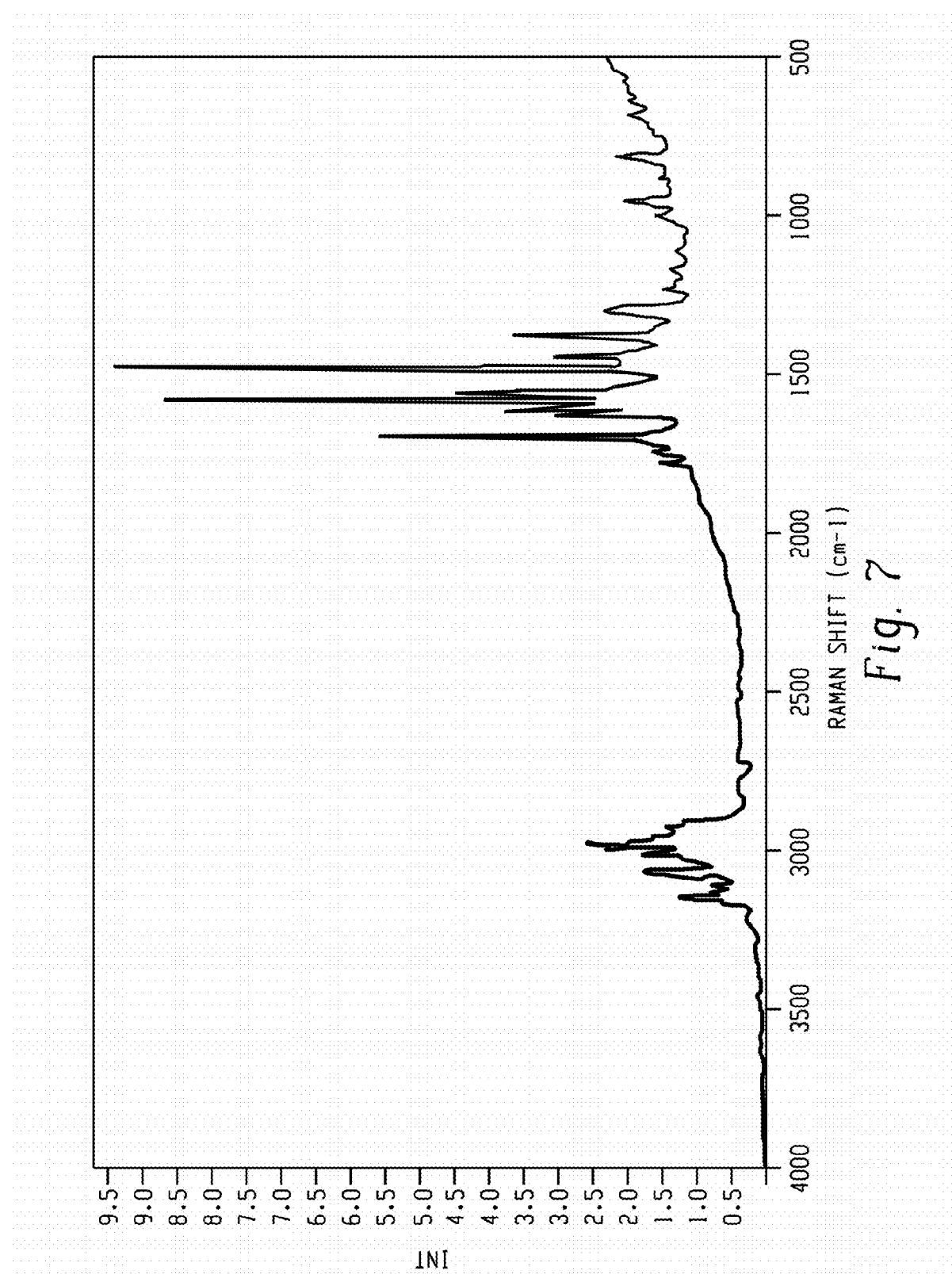
FIG. 7 is a graph of Raman intensity (arbitrary units) versus Raman shift ($cm^{-1}$) showing the FT-Raman spectrum of the first Polymorph A sample.
Figure 8:
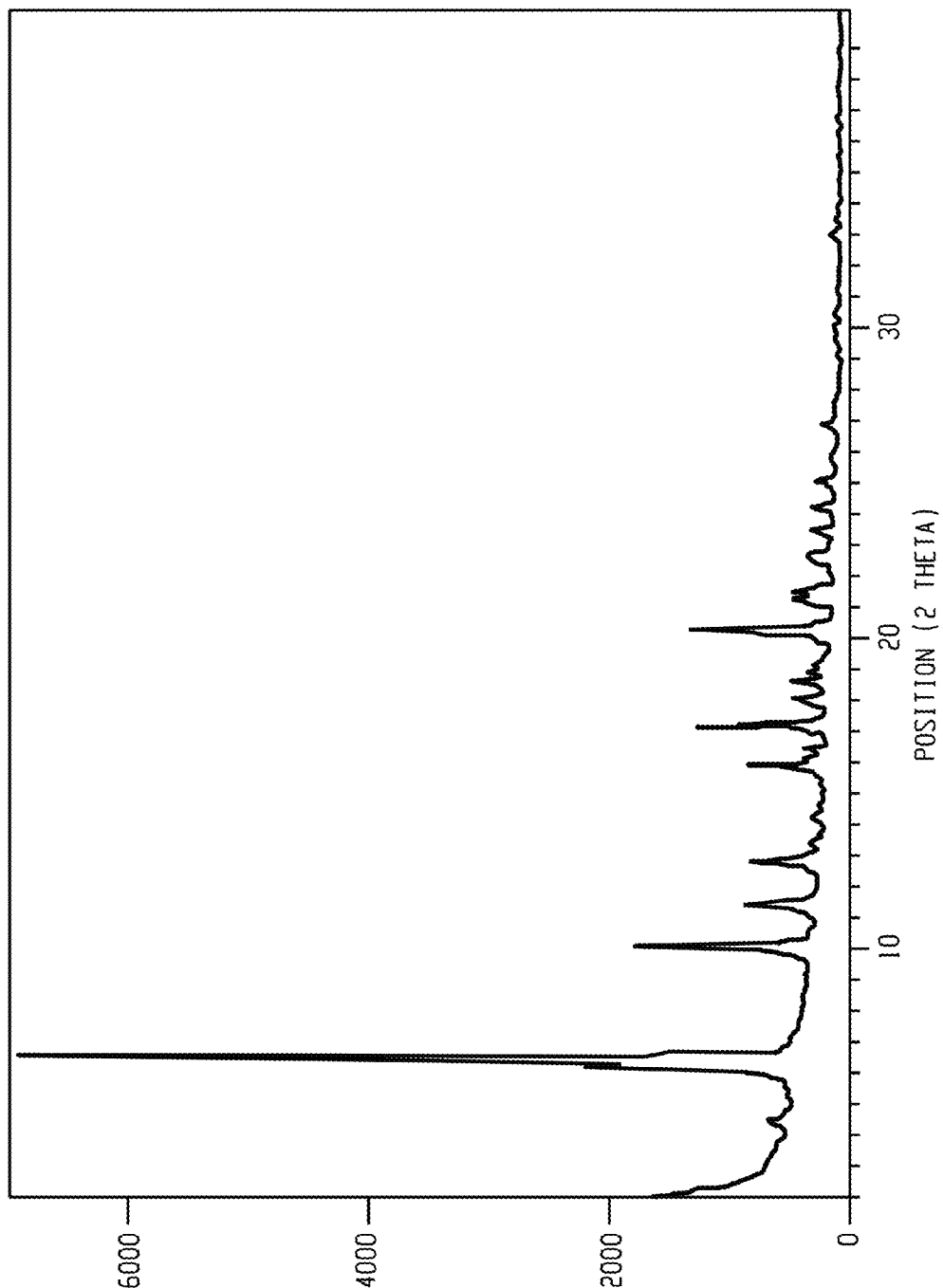
FIG. 8 is a graph of intensity (counts per second) versus scattering angle (degrees 2θ) showing the results of X-ray powder diffraction analysis of the first Polymorph A sample.

The Form A polymorph exhibits an X-ray powder diffraction pattern ("XRPD") having peak locations in accordance with FIG. 8. Polymorph A is characterized by an X-ray powder diffraction pattern obtained from a Cu Kα source which comprises peaks at 2θ values of 6.4, 16.3, 18.8, 21.8, and 23.7+/−0.2; or 10.1, 17.4, 20.5, 21.6, 23.0, and 24.5+/−0.2; or 11.6, 18.3, 21.6, 23.0, and 25.4+/−0.2. Polymorph A has a primary endotherm at 231.4° C. as determined by DSC. Polymorph A has a Raman spectrum with the characteristic values of FIG. 7.

Figure 12:
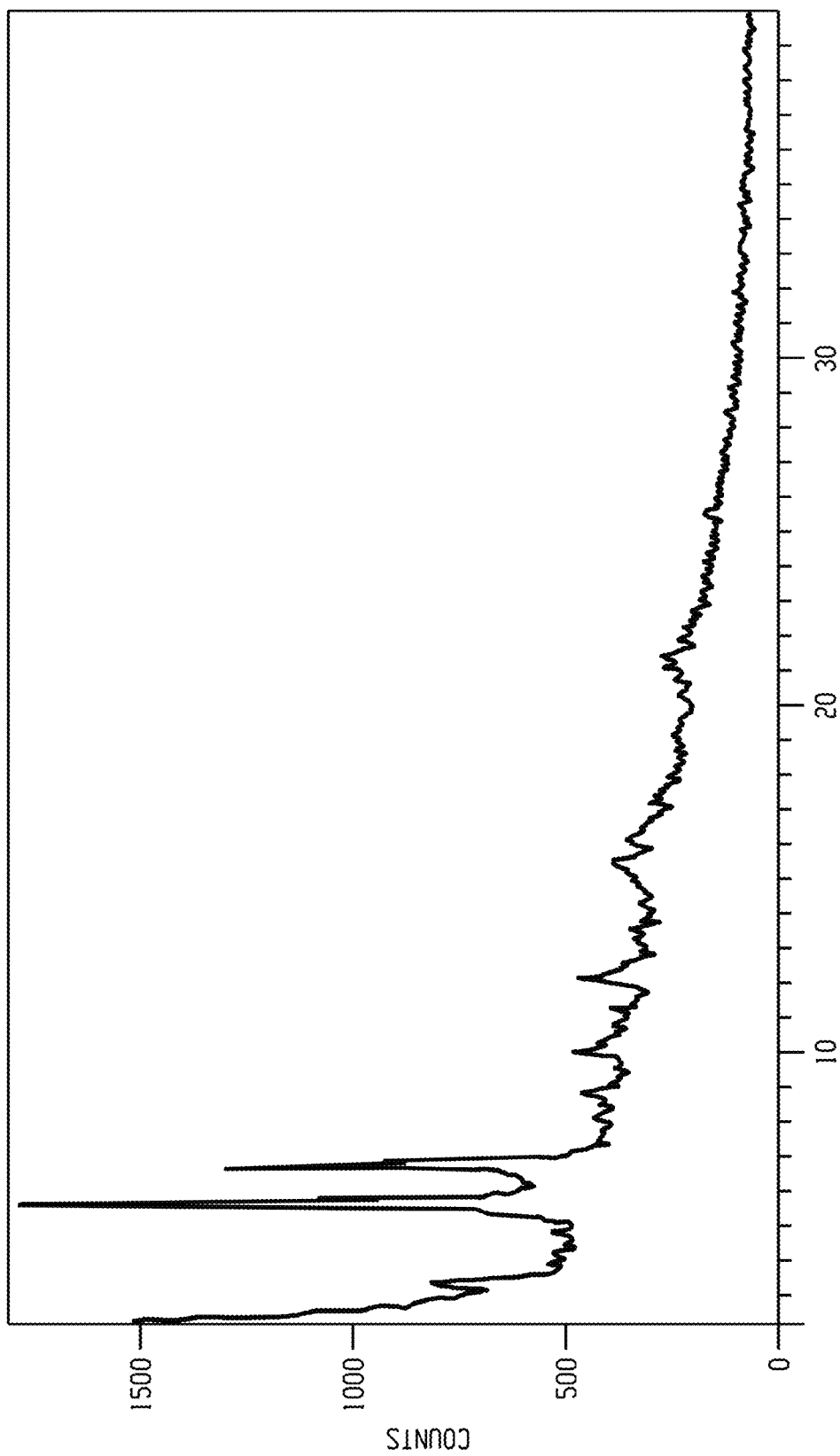
FIG. 12 is a graph of intensity (counts per second) versus scattering angle (degrees 2θ) showing the results of X-ray powder diffraction analysis of the first Polymorph B sample.

The Form B polymorph exhibits an X-ray powder diffraction pattern having peak locations in accordance with FIG. 12. Polymorph B is characterized by an X-ray powder diffraction pattern obtained from a Cu Kα source which comprises peaks at 2θ values of 5.6, 6.8, 10.3, and 12.2+/−0.2.

Figure 11:
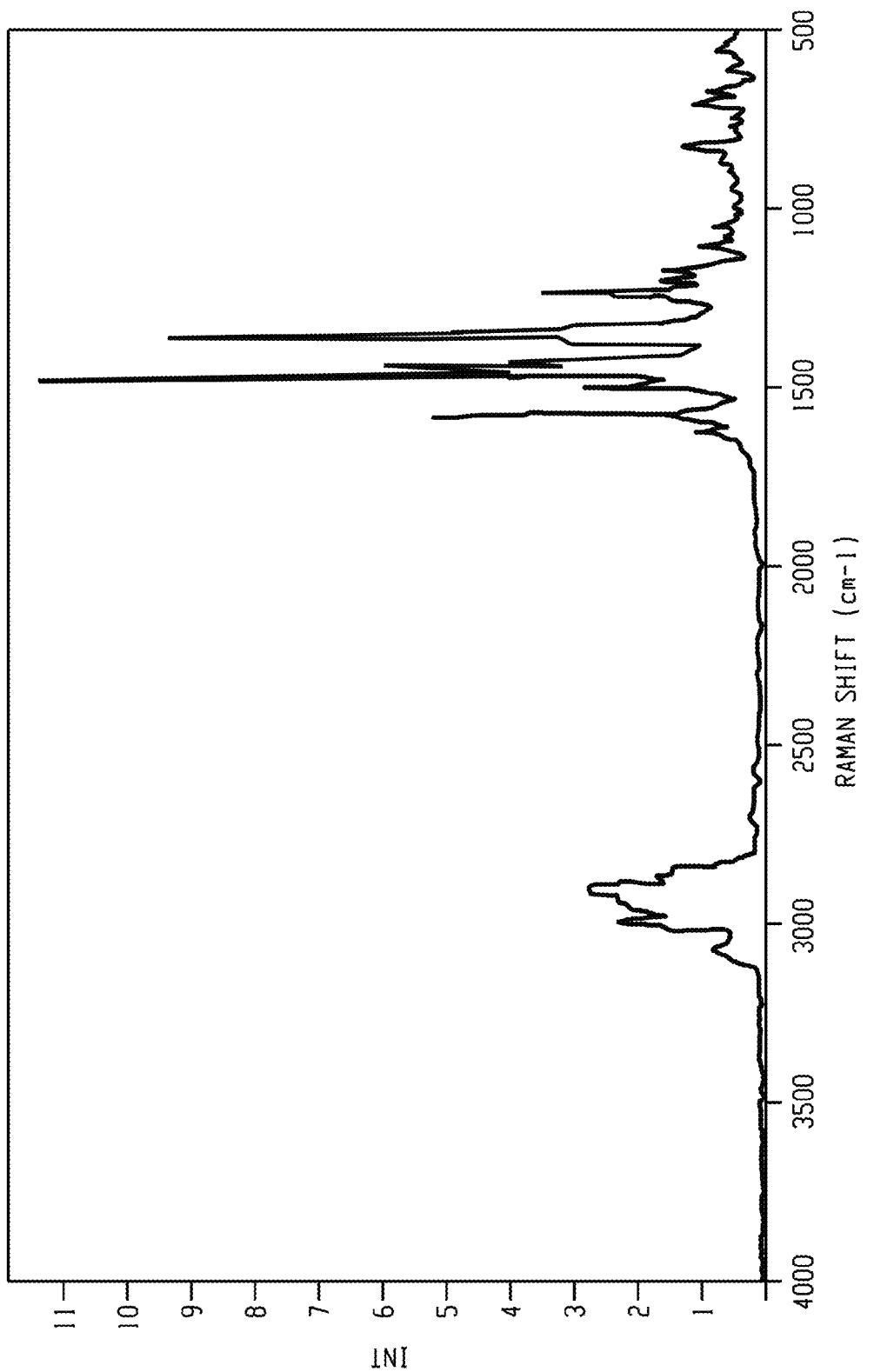
FIG. 11 is a graph of Raman intensity (arbitrary units) versus Raman shift ($cm^{-1}$) showing the FT-Raman spectrum of the first Polymorph B sample.

Polymorph B has a primary endotherm at 252° C. as determined by DSC. Polymorph B has a Raman spectrum with the characteristic values of FIG. 11.

Figure 15:
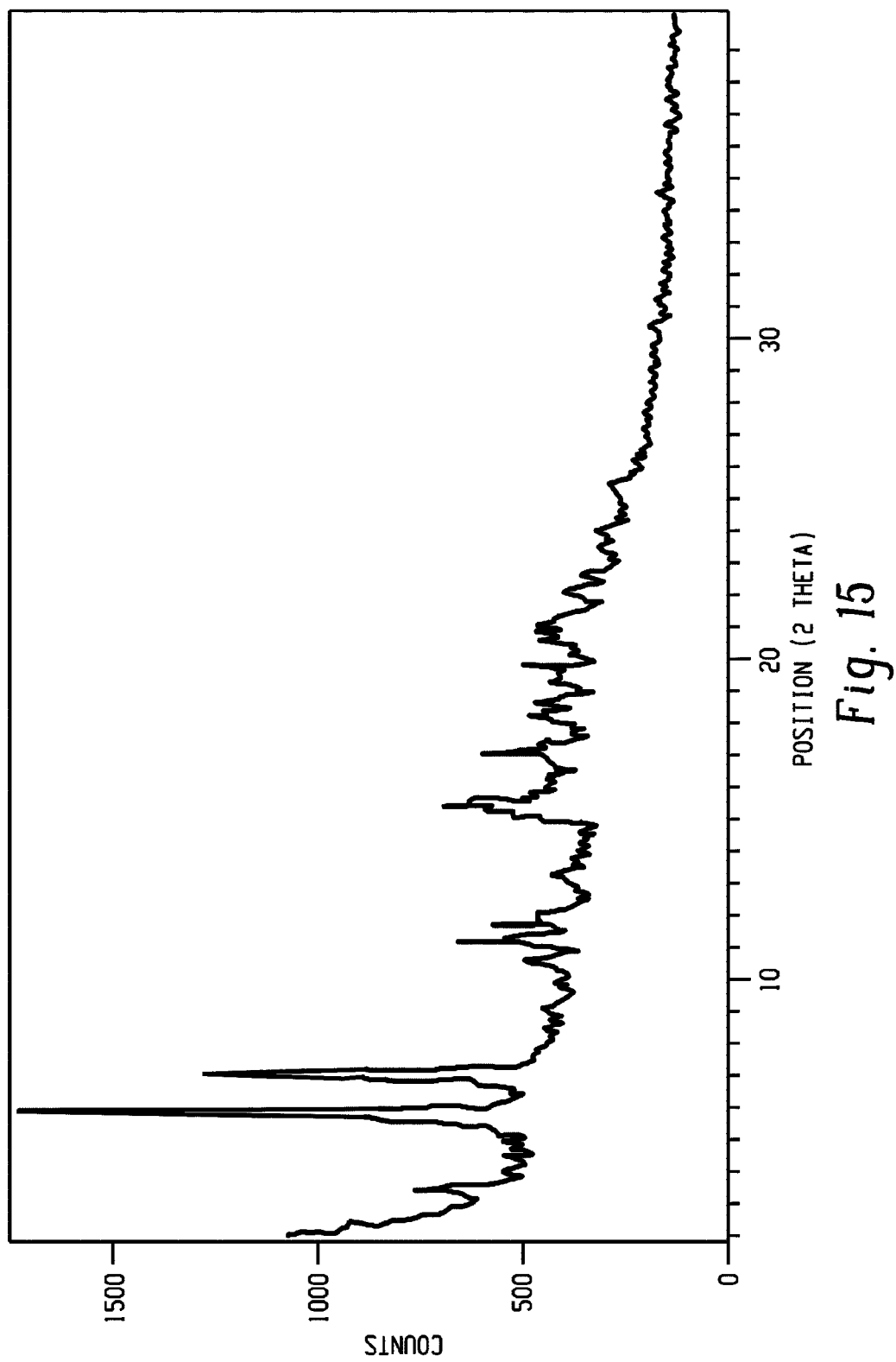
FIG. 15 is a graph of intensity (counts per second) versus scattering angle (degrees 2θ) showing the results of X-ray powder diffraction analysis of the Polymorph C sample.

The Form C polymorph exhibits an X-ray powder diffraction pattern having peak locations in accordance with FIG. 15. Polymorph C is characterized by an X-ray powder diffraction pattern obtained from a Cu Kα source which comprises peaks at 2θ values of 6.0, 11.6, 15.9, 18.6, and 21.3+/−0.2; or 7.2, 12.1, 17.3, and 20.2+/−0.2. Polymorph C has a primary endotherm at 82.6° C. as determined by DSC.

Figure 18:
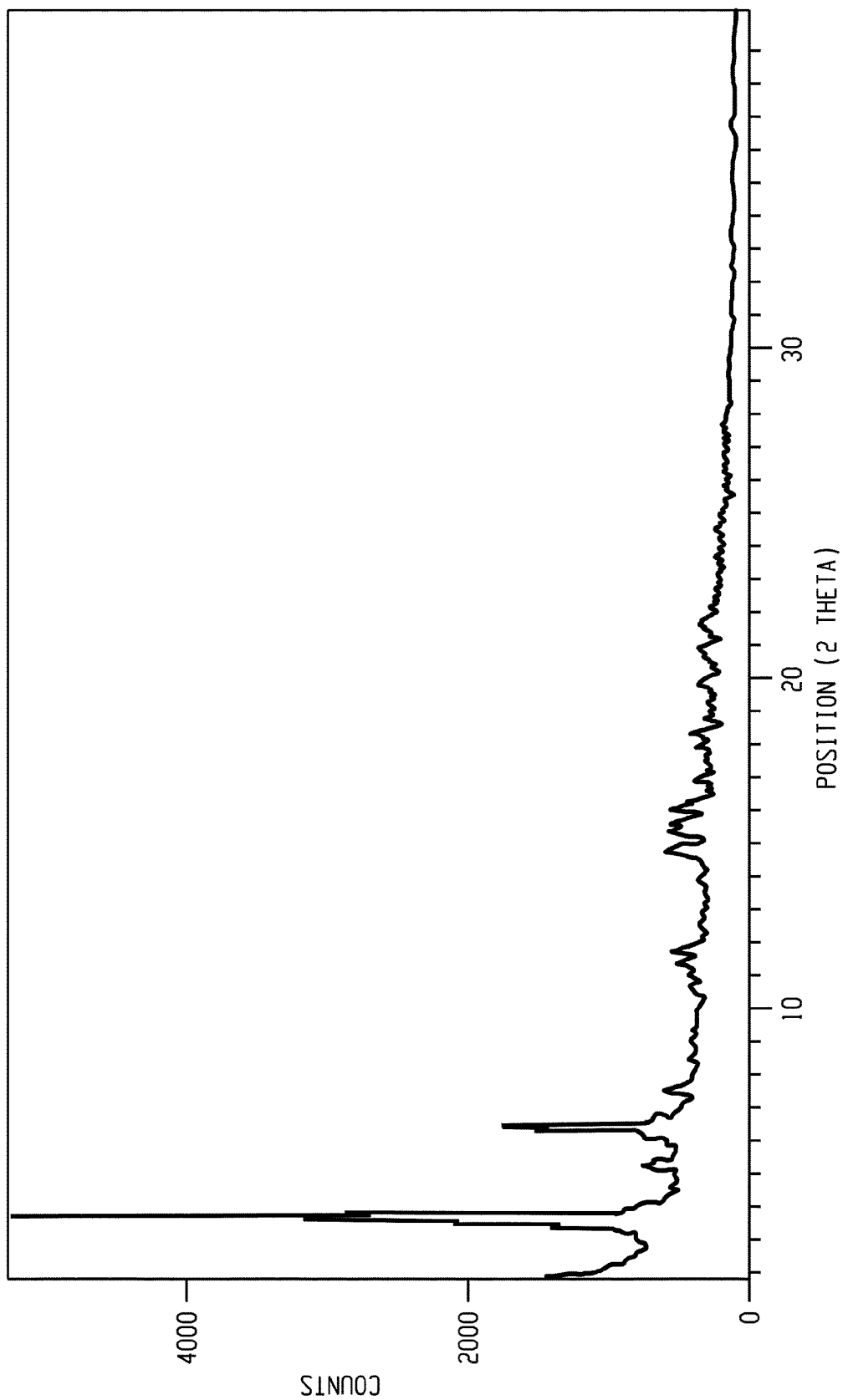
FIG. 18 is a graph of intensity (counts per second) versus scattering angle (degrees 2θ) showing the results of X-ray powder diffraction analysis of the Polymorph D sample.

The Form D polymorph exhibits an X-ray powder diffraction pattern having peak locations in accordance with FIG. 18. Polymorph D is characterized by an X-ray powder diffraction pattern obtained from a Cu Kα source which comprises peaks at 2θ values of 4.0, 8.0, 15.1, 16.4, 18.7, and 21.8+/−0.2; or 5.5, 11.6, 15.8, 17.3, and 20.1+/−0.2; or 6.7, 12.0, 16.0, 18.2, and 21.1+/−0.2. Polymorph D has a DSC showing multiple endotherms indicative of solvated form.

Figure 21:
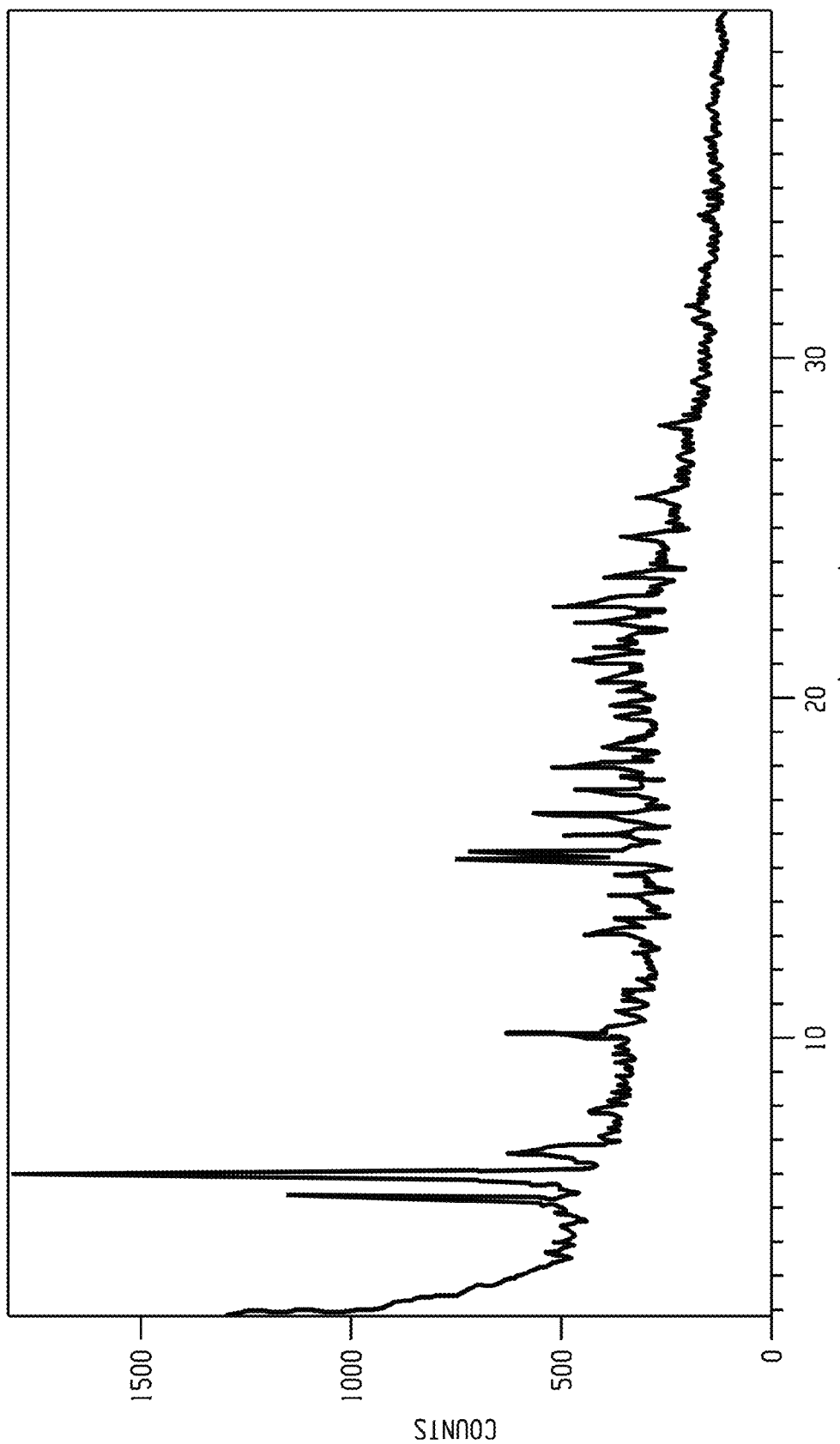
FIG. 21 is a graph of intensity (counts per second) versus scattering angle (degrees 2θ) showing the results of X-ray powder diffraction analysis of the Polymorph E sample.

The Form E polymorph exhibits an X-ray powder diffraction pattern having peak locations in accordance with FIG. 21. Polymorph E is characterized by an X-ray powder diffraction pattern obtained from a Cu Kα source which comprises peaks at 2θ values of 5.5, 10.3, 14.3, 15.8, 17.5, 19.0, 20.5, 21.7, and 23.8+/−0.2; or 6.2, 13.2, 14.9, 16.2, 18.2, 19.7, 20.8, 22.2, and 24.7+/−0.2; or 6.8, 13.6, 15.5, 16.9, 18.8, 20.0, 21.3, 22.8, and 25.8+/−0.2. Polymorph E has a DSC showing a broad endotherm below 100° C., indicative of solvated form.

Figure 24:
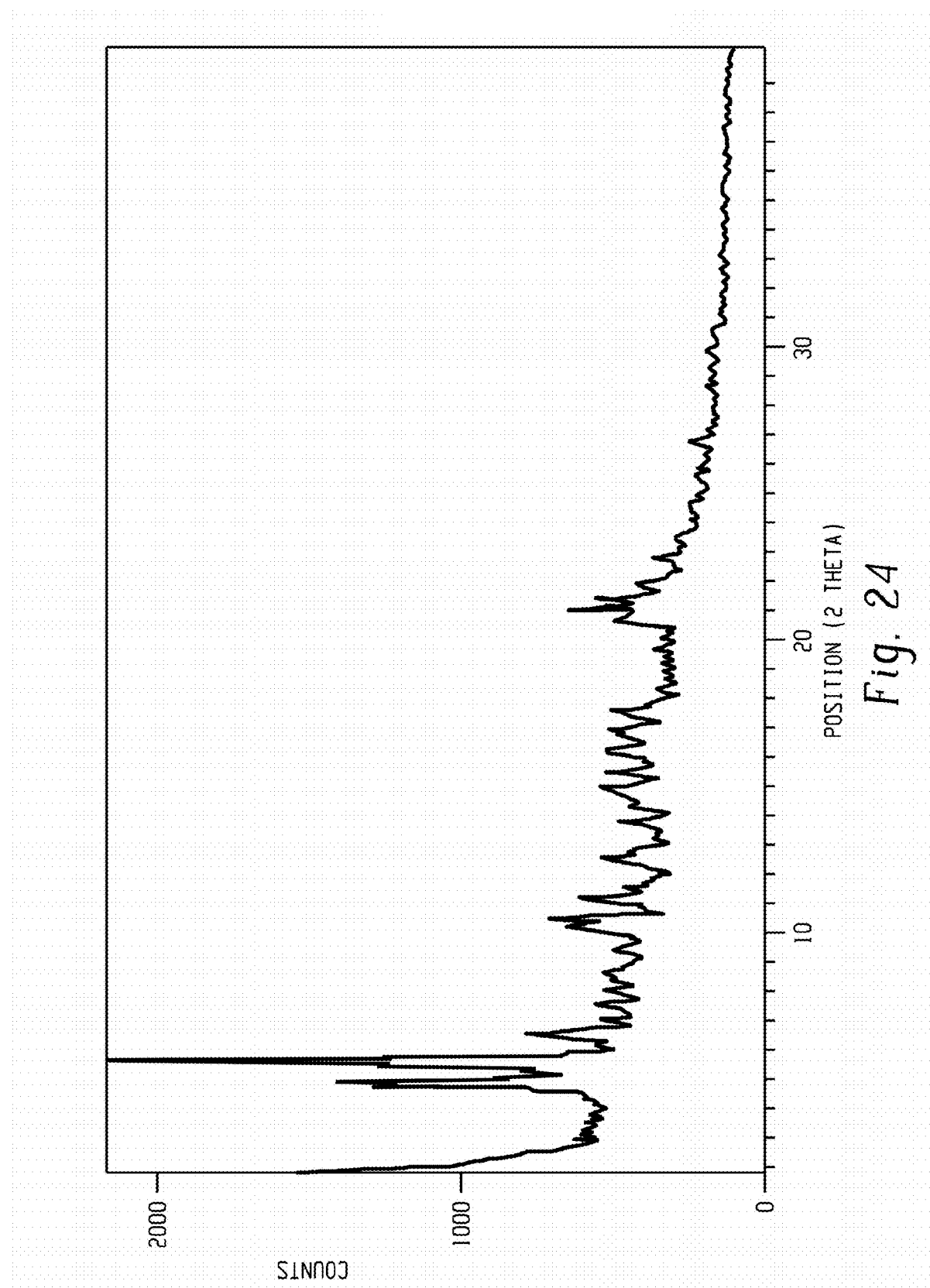
FIG. 24 is a graph of intensity (counts per second) versus scattering angle (degrees 2θ) showing the results of X-ray powder diffraction analysis of the Polymorph F sample.

The Form F polymorph exhibits an X-ray powder diffraction pattern having peak locations in accordance with FIG. 24. Polymorph F is characterized by an X-ray powder diffraction pattern obtained from a Cu Kα source which comprises peaks at 2θ values of 5.2, 7.9, 10.4, 11.7, 14.9, 17.0, and 21.1+/−0.2; or 5.8, 8.2, 10.6, 12.8, 15.7, 17.8, and 21.6+/−0.2; or 6.7, 9.0, 11.4, 13.8, 16.4, and 20.0+/−0.2. Polymorph F has a primary endotherm at 111.7° C. as determined by DSC.

Figure 27:
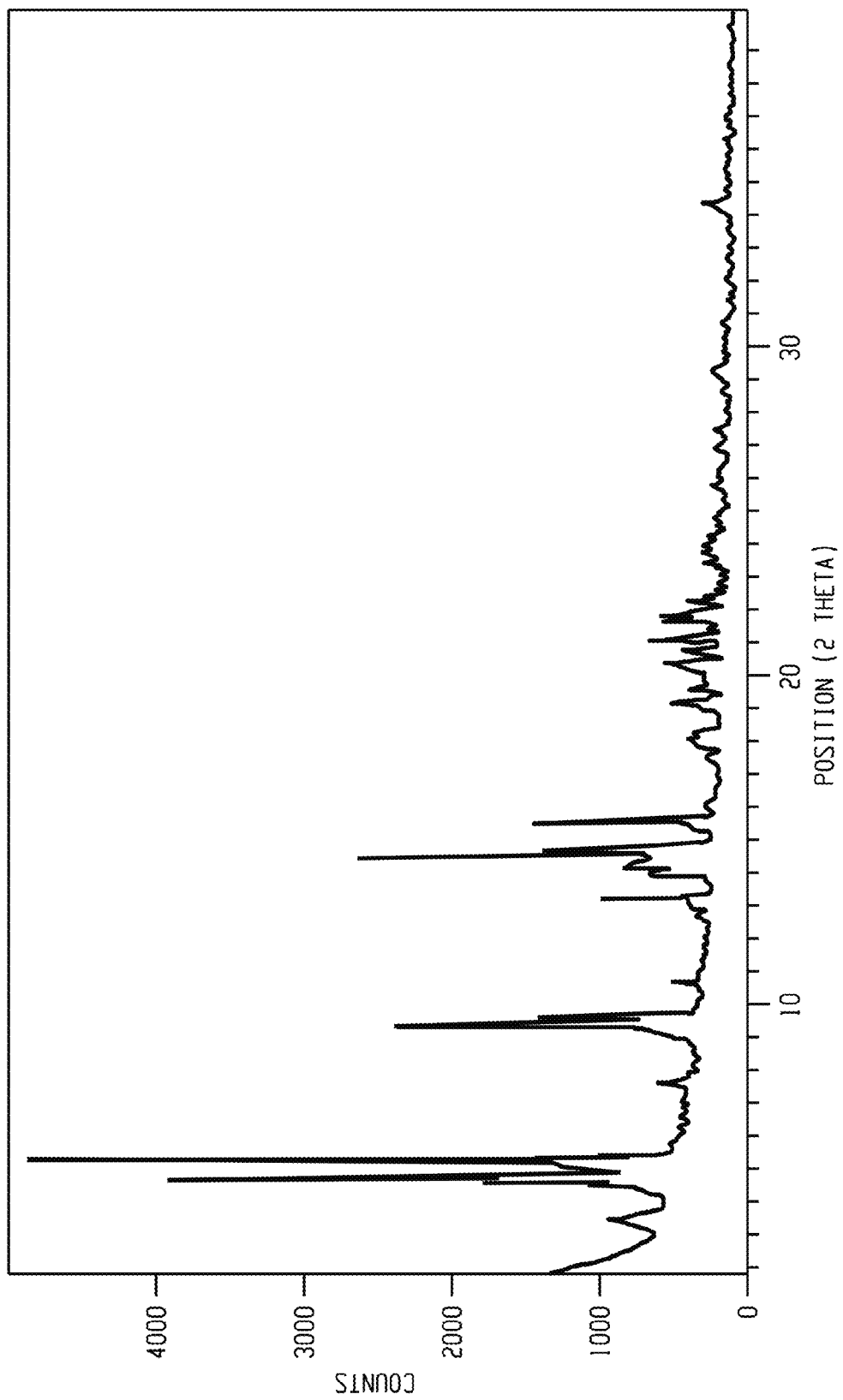
FIG. 27 is a graph of intensity (counts per second) versus scattering angle (degrees 2θ) showing the results of X-ray powder diffraction analysis of the Group G sample.

The Form G polymorph exhibits an X-ray powder diffraction pattern having peak locations in accordance with FIG. 27. Polymorph G is characterized by an X-ray powder diffraction pattern obtained from a Cu Kα source which comprises peaks at 2θ values of 5.0, 9.5, 13.4, 15.0, 19.2, 20.9, and 22.5+/−0.2; or 5.5, 9.8, 14.2, 15.7, 19.9, and 21.4+/−0.2; or 7.8, 10.9, 14.7, 18.4, 20.6, and 22.0+/−0.2. Polymorph G has a primary endotherm at 284.3° C. as determined by DSC.

Figure 30:
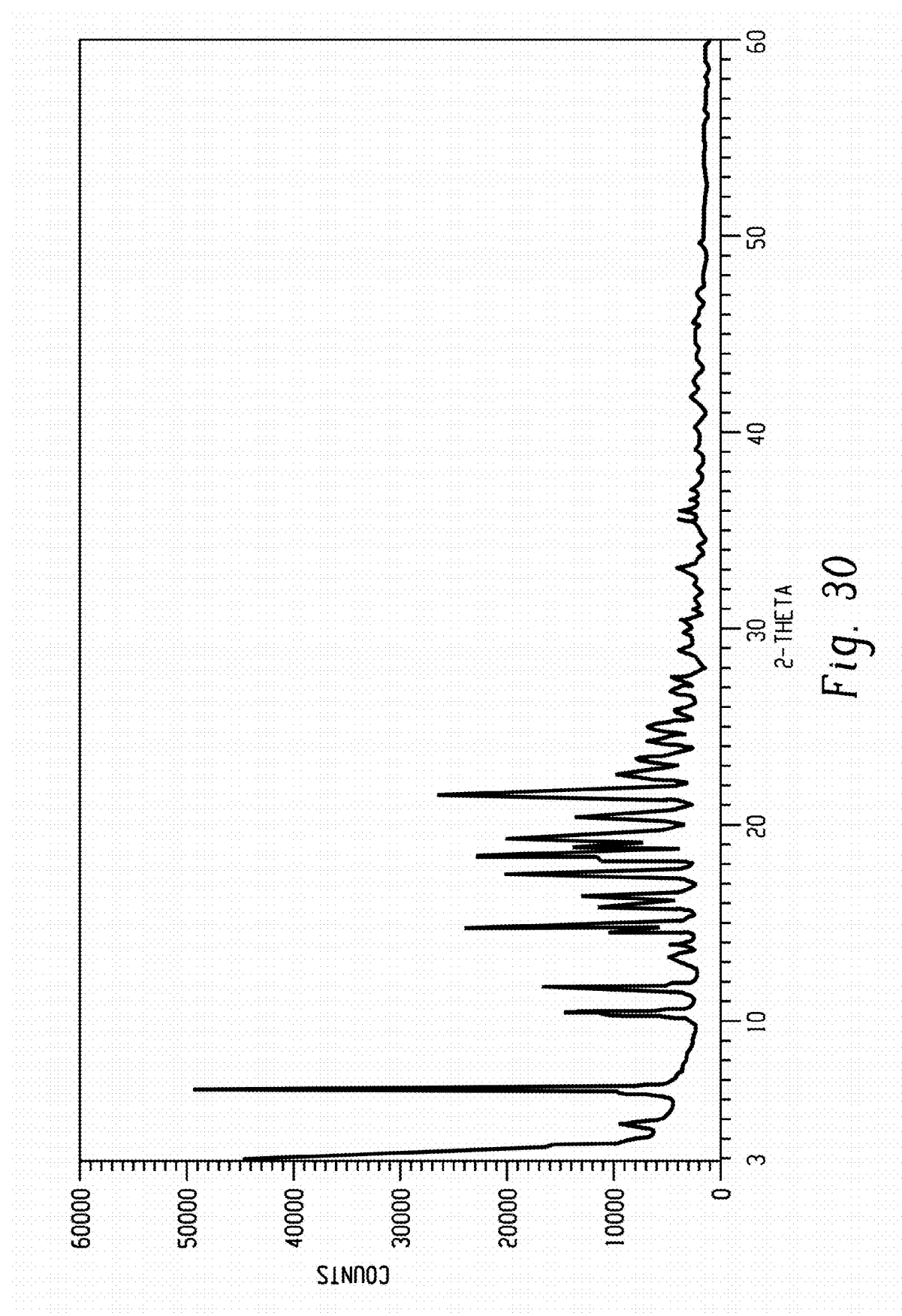
FIG. 30 is a graph of intensity (counts per second) versus scattering angle (degrees 2θ) showing the results of X-ray powder diffraction analysis of the Polymorph H sample.

The Form H polymorph exhibits an X-ray powder diffraction pattern having peak locations in accordance with FIG. 30. Polymorph H is characterized by an X-ray powder diffraction pattern obtained from a Cu Kα source which comprises peaks at 2θ values of 6.5, 13.1, 15.0, 17.5, 20.4, 22.6, 25.2, 27.6, and 30.7; or 10.3, 13.8, 15.7, 18.4, 20.7, 22.9, 26.0, 29.1, and 32.5; or 11.7, 14.6, 16.4, 19.4, 21.7, 24.5, 27.0, 30.0, and 33.1+/−0.2.

Figure 31:
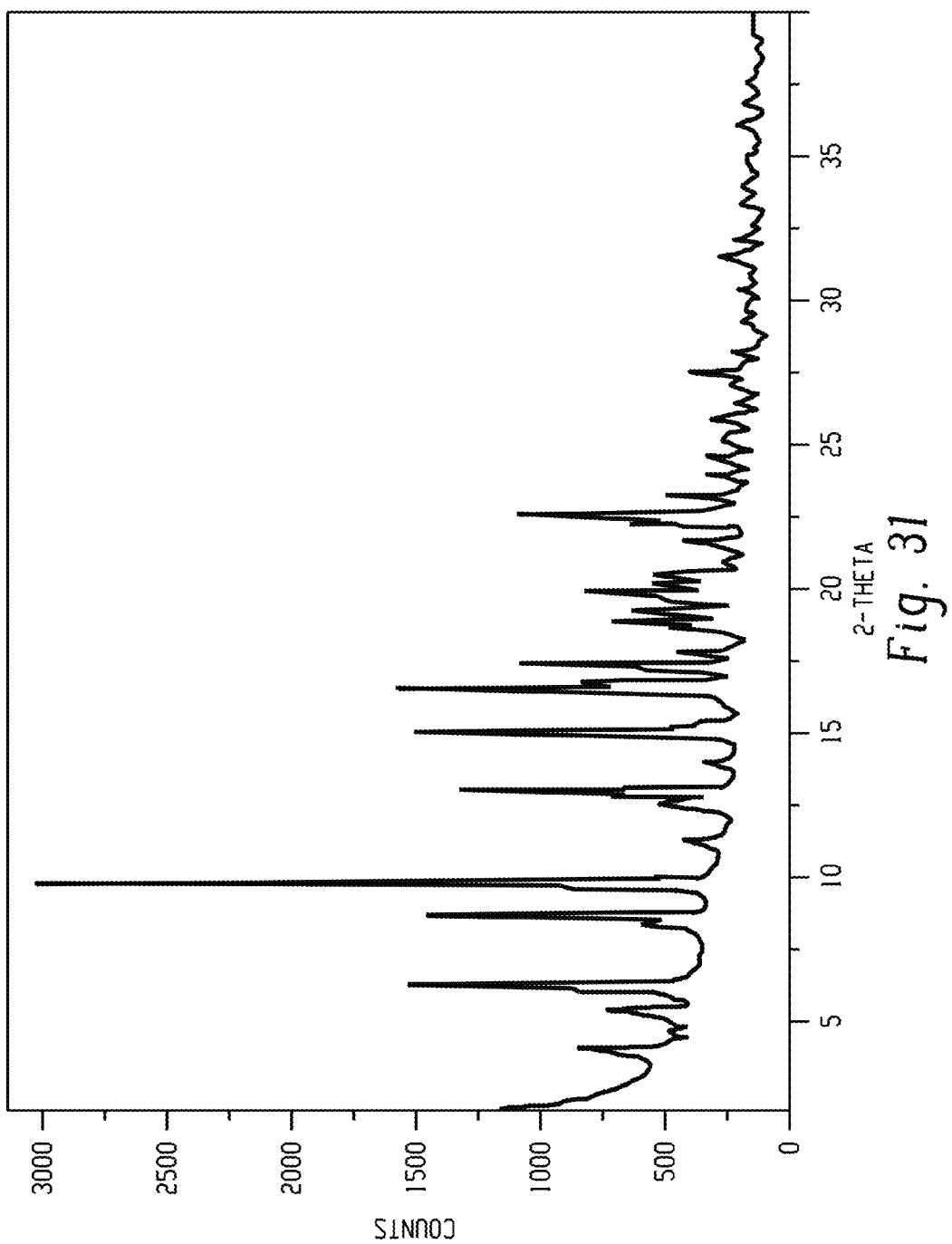
FIG. 31 is a graph of intensity (counts per second) versus scattering angle (degrees 2θ) showing the results of X-ray powder diffraction analysis of the Polymorph I sample.
Figure 33:
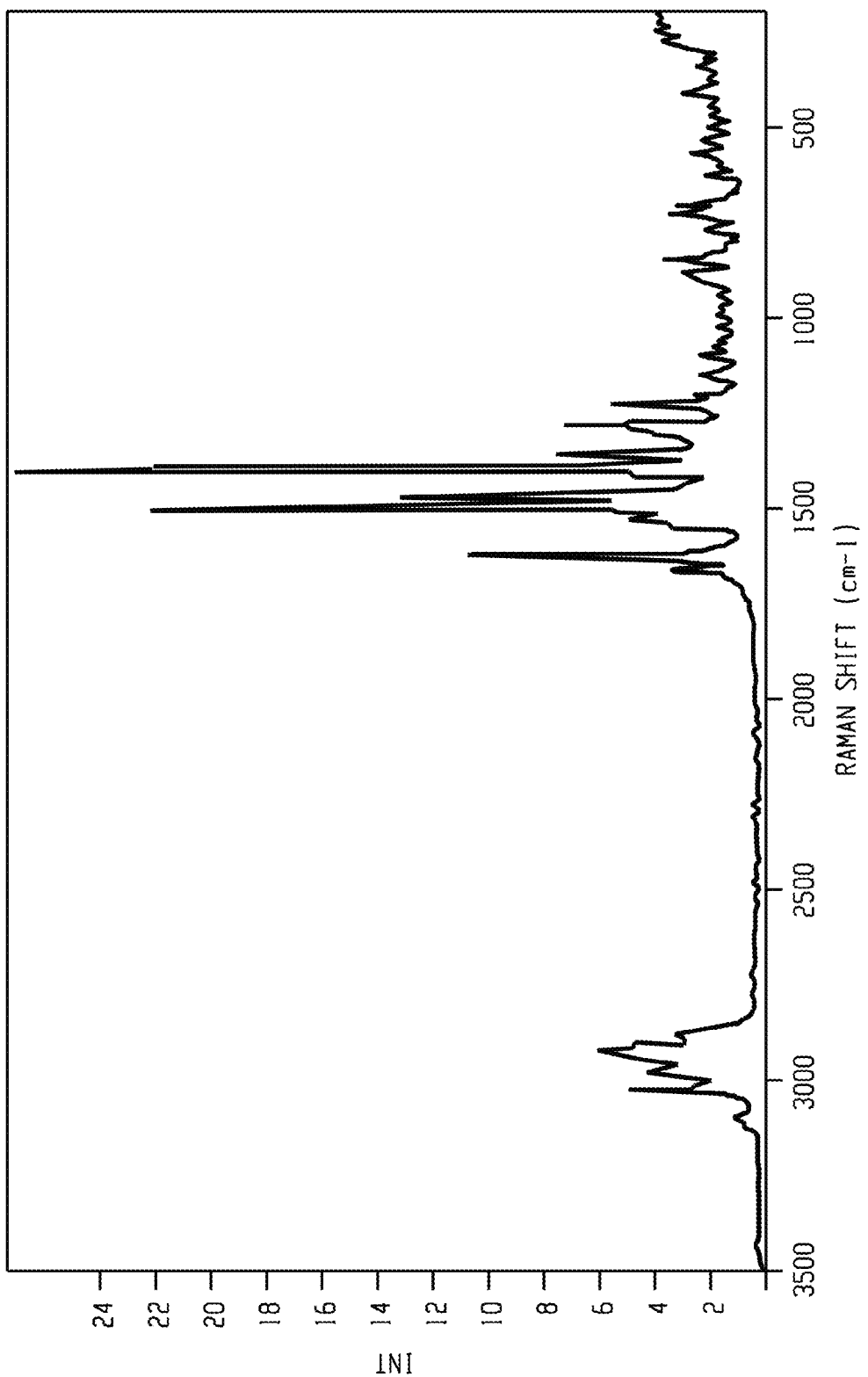
FIG. 33 is a graph of Raman intensity (arbitrary units) versus Raman shift (cm$^{-1}$) showing the FT-Raman spectrum of the Polymorph I sample.

The Form I polymorph exhibits an X-ray powder diffraction pattern having peak locations in accordance with FIG. 31. Polymorph I is characterized by an X-ray powder diffraction pattern obtained from a Cu Kα source which comprises peaks at 2θ values of 4.2, 8.3, 12.9, 14.1, 16.9, 18.1, 19.5, 21.2, 22.9, and 24.9; or 5.4, 8.6, 13.0, 15.4, 17.1, 18.7, 20.5, 22.2, 24.2, and 26.1; or 6.5, 9.8, 13.7, 15.6, 17.8, 19.2, 20.9, 22.6, 24.7, and 27.8+/−0.2. Polymorph I has a primary endotherm of 200.9° C. as determined by DSC. Polymorph I has a Raman spectrum with the characteristic values of FIG. 33.

Also disclosed herein is a composition comprising a crystalline sodium salt of ACH-0142684, wherein at least 90% of the crystalline sodium salt of ACH-0142684 is the Form A polymorph, the Form B polymorph, the Form C polymorph, the Form D polymorph, the Form E polymorph, the Form F polymorph, the Form G polymorph, the Form H polymorph, the Form I polymorph, or a combination thereof. The composition may also contain a pharmaceutically acceptable carrier, which can be any pharmaceutically acceptable excipient such as a binder, filler, lubricant, solvent, disintegrant or coating.

The sodium salt of ACH-0142684 is generally present within a pharmaceutical composition in a therapeutically effective amount. As used herein, a "therapeutically effective amount" (or dose) is an amount that, upon administration to a patient, results in a discernible patient benefit. It will be apparent that the therapeutically effective amount will depend upon the particular patient, the indication for which it is administered, as well as the effects of any co-administered drugs.

In an embodiment the composition may be suitable for pharmaceutical use and may be in the form of a pharmaceutical composition. The pharmaceutical composition may have any suitable form, and may be a tablet, capsule, solution, suspension, or a combination thereof.

The pharmaceutical composition may be used to treat a disorder, e.g., HCV. Therapeutic methods provided herein may be used to treat an existing disorder, or to prevent, decrease the severity of, or delay the onset of a disorder in a patient. Alternatively, or in addition, compounds provided herein may be administered to a patient to prevent infection in a healthy patient. Patients include humans, domesticated companion animals (pets, e.g., dogs) and livestock animals. A method for treating a disorder may comprise administering to a patient in need of treatment a therapeutically effective amount of the pharmaceutical composition.

Pharmaceutical compositions may be packaged or used for the manufacture of a medicament for treatment. Packaged pharmaceutical preparations include a container holding a therapeutically effective amount of the sodium salt of ACH-0142684 and may further include labeling (e.g., instructions) indicating that the contained composition is to be used for treating the disorder.

This disclosure is further illustrated by the following examples that should not be construed as limiting.

EXAMPLES

Instrumental Techniques

The following instrumental techniques are used for analysis of all crystal forms unless otherwise noted.

X-Ray Powder Diffraction (PXRD)

PXRD diffractograms were acquired using either a Bruker D8 Discovery diffractometer with a HI-STAR GADDS detector or PANalytical X'Pert Pro diffractometer on Si zero-background wafers. All diffractograms were collected using Cu Kα (45 kV/40 mA) radiation and a step size of 0.02° 2θ unless noted otherwise.

Differential Scanning Calorimetry (DSC)

DSC was conducted with a TA Instruments Q100 differential scanning calorimeter equipped with an autosampler and a refrigerated cooling system under 40 mL/min $N_2$ purge. DSC thermograms were obtained at 15° C./min in crimped Al pans.

Thermogravimetric Analysis (TGA)

TGA thermograms were obtained with a TA Instruments Q500 thermogravimetric analyzer under 40 mL/min $N_2$ purge at 15° C./min in Pt or Al pans.

Thermogravimetric Analysis with IR Off-Gas Detection (TGA-IR)

TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min $N_2$ flow and heating rate of 15° C./min in Pt or Al pans. IR spectra were collected at 4 $cm^{-1}$ resolution and 32 scans at each time point.

FT-Raman Spectroscopy

Raman spectra were collected with a Nicolet NXR9650 or NXR 960 spectrometer (Thermo Electron) equipped with 1,064 nm $Nd:YVO_4$ excitation laser, InGaAs and liquid-$N_2$ cooled Ge detectors, and a MicroStage. All spectra were acquired at 4 $cm^{-1}$ resolution, 64-128 scans, using Happ-Genzel apodization function and 2-level zero-filling, unless noted otherwise.

Example 1

Solubility Assessment of ACH-0142684

The solubility of ACH-0142684 sodium salt was determined at room temperature using the following procedure. The input material (~10 mg) was weighed into each of 12 vials, followed by addition of a solvent in multiple aliquots between 50µL to 10-mL at room temperature. Samples were visually inspected for complete dissolution after each solvent addition. The solubility of crystalline ACH-0142684 sodium salt is summarized in TABLE 1, which provides a solubility assessment of amorphous API in 12 solvents. The solubility of API-0142684 in water after temperature cycling between 40° C. and 5° C. for 2 days is ~50 mg/ml.

TABLE 1

| Solvent | Solubility (mg/mL) |
| --- | --- |
| Water | <0.99[1] |
| MeOH | 92-123 |
| IPA | 1.1-1.3 |
| ACN | 1.0-1.2 |
| THF | 9.2-18.4 |
| DCM | 49-98 |
| EtOAc | <1.02 |
| MTBE | <0.93 |
| acetone | 5.7-14 |
| Toluene | <1.04 |
| DMSO | 97-129 |
| TFE | 100-133 |

Example 2

Screen Design

A diverse set of crystallization experiments included temperature-cycled ripening of API slurries, cooling, and evaporative experiments in 48 solvents/solvent mixtures and 10 vapor diffusion experiments.

Solvent Selection

The list of 48 solvents and aqueous mixtures used for the screen are shown in TABLE 2. They were selected based on a diverse range of properties including dielectric constants, boiling points, and H-bonding that are important to crystallization and crystal-form discovery. The values in TABLE 2 are derived from ACH-0142684 loading in solvent and dissolution. The symbol † indicates the solubility value is found in TABLE 1.

TABLE 2

| No. | Solvent | Solubility (mg/mL) |
| --- | --- | --- |
| 1 | Water | † |
| 2 | MeOH | † |
| 3 | 2-Methoxyethanol | >93 |
| 4 | 1-Propanol | <50 |
| 5 | Nitromethane | <50 |
| 6 | ACN | † |
| 7 | DMSO | † |
| 8 | Acetone | † |
| 9 | 2-Butanone | <50 |
| 10 | Dichloromethane | † |
| 11 | MeOAc | <50 |
| 12 | 4-Methyl-2-pentanone | <50 |
| 13 | Chloroform | >153 |
| 14 | EtOAc | † |
| 15 | Chlorobenzene | <50 |
| 16 | THF | † |
| 17 | 1,4-Dioxane | <50 |
| 18 | Isopropyl ether | <50 |
| 19 | Toluene | † |
| 20 | Cyclohexane | <50 |
| 21 | Pentane | <50 |
| 22 | 1-Butanol | <50 |
| 23 | IPA | † |
| 24 | TFE | † |
| 25 | Dimethyl Carbonate | <50 |
| 26 | MTBE | † |
| 27 | Isopropyl acetate | <50 |
| 28 | EtOH | <72 |
| 29 | 1-Methoxy-2-propanol | >80 |
| 30 | Cyclohexanone | >87 |
| 31 | DMF | >93 |
| 32 | 2-Methoxyethyl ether | <90 |
| 33 | Methanol: 5 vol % Water | >177 |
| 34 | Acetonitrile: 5 vol % Water | <50 |
| 35 | Acetone: 5 vol % Water | <50 |
| 36 | THF: 5 vol % Water | >85 |
| 37 | 2-propanol: 5 vol % Water | <50 |
| 38 | Methanol: 10 vol % Water | >85 |
| 39 | Acetonitrile: 10 vol % | <50 |
| 40 | Acetone: 10 vol % Water | <99 |
| 41 | THF: 10 vol % Water | >107 |
| 42 | Dioxane: 10 vol % Water | >93 |
| 43 | 2-propanol: 10 vol % | <50 |
| 44 | Acetone: 20 vol % Water | <96 |
| 45 | 2-propanol: 20 vol % Water | <95 |
| 46 | EtOAc:Pentane (1:1) | <50 |
| 47 | EtOAc:Pentane (1:4) | <50 |
| 48 | EtOAc:Pentane (1:10) | <50 |

Example 3

Crystallization Screening

Crystallization experiments were conducted in 48 solvents and aqueous mixtures using the following three crystallization modes:

Temperature-cycled ripening of API slurries between 5-40° C. for 48 hours;

Cooling of saturated solutions prepared at RT to 5° C. (24 hours);

Slow evaporation of saturated solutions at RT. In addition, 10 vapor diffusion experiments were also conducted (Table 4) at RT. These solvent systems were selected based on API solubility, and the miscibility and boiling points of solvents and anti-solvents.

Screen Results

All solid outputs from the screen were isolated and analyzed by FT-Raman spectroscopy and/or PXRD. The samples were then sorted into polymorphs based on Raman spectral match. Representative samples from each of the polymorphs were further analyzed by additional techniques (PXRD, DSC, TGA-IR, PLM, etc.) as appropriate and as sample quantity permitted. These data were used to support the form assignment.

The results are summarized in TABLES 3 and 4. Characterization data and more detailed discussion of the different crystal forms are summarized in the following sections. In TABLES 3 and 4, A, B, C, D, or E, etc. indicates the respective crystalline polymorph obtained. "Amorphous" indicates an amorphous solid was obtained, (-) indicates the experiment was not performed, and a blank space indicates no solid was obtained. The screening study led to one hydrated form (Polymorph A) and multiple solvated forms (Polymorph s B-E). The majority of the screening studies led to Polymorph A, indicating that this form is the most stable form at the crystallization conditions studied.

TABLE 1

Form Assignment of Screening Samples

| Sample # | Solvent | Temperature Cycling | Evaporation | Cooling |
|---|---|---|---|---|
| 1 | Water | | Amorphous | |
| 2 | Methanol | Other | — | — |
| 3 | 2-Methoxyethanol | | Amorphous | |
| 4 | 1-Propanol | A | Amorphous | |
| 5 | Nitromethane | A | | |
| 6 | Acetonitrile | A | Amorphous | |
| 7 | Dimethylsulfoxide | | E | |
| 8 | Acetone | A | Amorphous | |
| 9 | 2-Butanone | A | Amorphous | |
| 10 | Dichloromethane | A | | |
| 11 | Methyl acetate | A | Amorphous | |
| 12 | 4-Methyl-2-pentanone | A | | |
| 13 | Chloroform | | Amorphous | |
| 14 | Ethyl acetate | A | | |
| 15 | Chlorobenzene | A | Amorphous | |
| 16 | Tetrahydrofuran | B | Amorphous | |
| 17 | 1,4-Dioxane | B | Amorphous | |
| 18 | Isopropyl ether | A plus amorphous | | |
| 19 | Toluene | A | | |
| 20 | Cyclohexane | Amorphous | | |
| 21 | Pentane | Amorphous | | |
| 22 | 1-Butanol | A plus amorphous | Amorphous | |
| 23 | 2-Propanol | A | Amorphous | |
| 24 | Trifluoroethanol | | Amorphous | |
| 25 | Dimethyl carbonate | A | | |
| 26 | t-Butyl methyl ether | Other | | |
| 27 | Isopropyl acetate | A | | |
| 28 | Ethanol | A | A | |
| 29 | 1-Methoxy-2-propanol | | Amorphous | C |
| 30 | Cyclohexanone | | Amorphous | |
| 31 | DMF | | Amorphous | |
| 32 | 2-Methoxyethyl ether | A | Amorphous | |
| 33 | Methanol: 5 vol % water | | Amorphous | |
| 34 | Acetonitrile: 5 vol % water | A | Amorphous | |
| 35 | Acetone: 5 vol % water | A | Amorphous | |
| 36 | THF: 5 vol % water | | Amorphous | |
| 37 | 2-Propanol: 5 vol % water | A | Amorphous | |
| 38 | Methanol: 10 vol % water | | Amorphous | |
| 39 | Acetonitrile: 10 vol % water | A | Amorphous | |
| 40 | Acetone: 10 vol % water | A | Amorphous | |
| 41 | THF: 10 vol % water | | Amorphous | |
| 42 | Dioxane: 10 vol % water | | B | |
| 43 | 2-Propanol: 10 vol % water | A | Amorphous | |
| 44 | Acetone: 20 vol % water | A | Amorphous | |
| 45 | 2-Propanol: 20 vol % water | A | Amorphous | |
| 46 | Ethyl acetate/pentane 1:1 | A | | |
| 47 | Ethyl acetate/pentane 1:4 | A | | |
| 48 | Ethyl acetate/pentane 1:10 | A plus amorphous | | |

TABLE 4

Results from Vapor Diffusion Mode of Crystallization

| Number | Solvent | Antisolvent | Polymorph |
|---|---|---|---|
| 1 | 2-Methoxyethanol | Ethyl acetate | |
| 2 | 2-Methoxyethanol | Isopropyl ether | A |
| 3 | Dimethylsulfoxide | Isopropyl ether | |
| 4 | Dimethylsulfoxide | Methyl acetate | |
| 5 | DMF | Ethyl acetate | |
| 6 | DMF | t-Butyl methyl ether | |
| 7 | Cyclohexanone | Pentane | D |
| 8 | Cyclohexanone | t-butyl methyl ether | Amorphous |
| 9 | Trifluoroethanol | Ethyl acetate | A |
| 10 | Trifluoroethanol | Isopropyl ether | Amorphous |

Example 4

Polymorph A (Hydrate)

Polymorph A was isolated from majority of the screening experiments. A total of 32 samples isolated from a variety of solvents and crystallization conditions (temperature cycling, evaporation and vapor diffusion) led to Polymorph A indicative of a stable form at/around room temperature.

Polymorph A was prepared on a 2.2-g scale using the following procedure: Acetonitrile: 5% water (60 mL) was added to the amorphous API (2,195.42 mg). The suspension was stirred at room temperature for an hour. The temperature of the suspension was then cycled between 40° C. and 5° C. for 24 hours with an hour hold at temperature limits. The suspension was then isolated by vacuum filtration and air-dried for an hour. The crystalline solids were then dried in a vacuum oven at 55° C. overnight to yield 1,803.64 mg of the hydrated form (Polymorph A).

Figure 9:
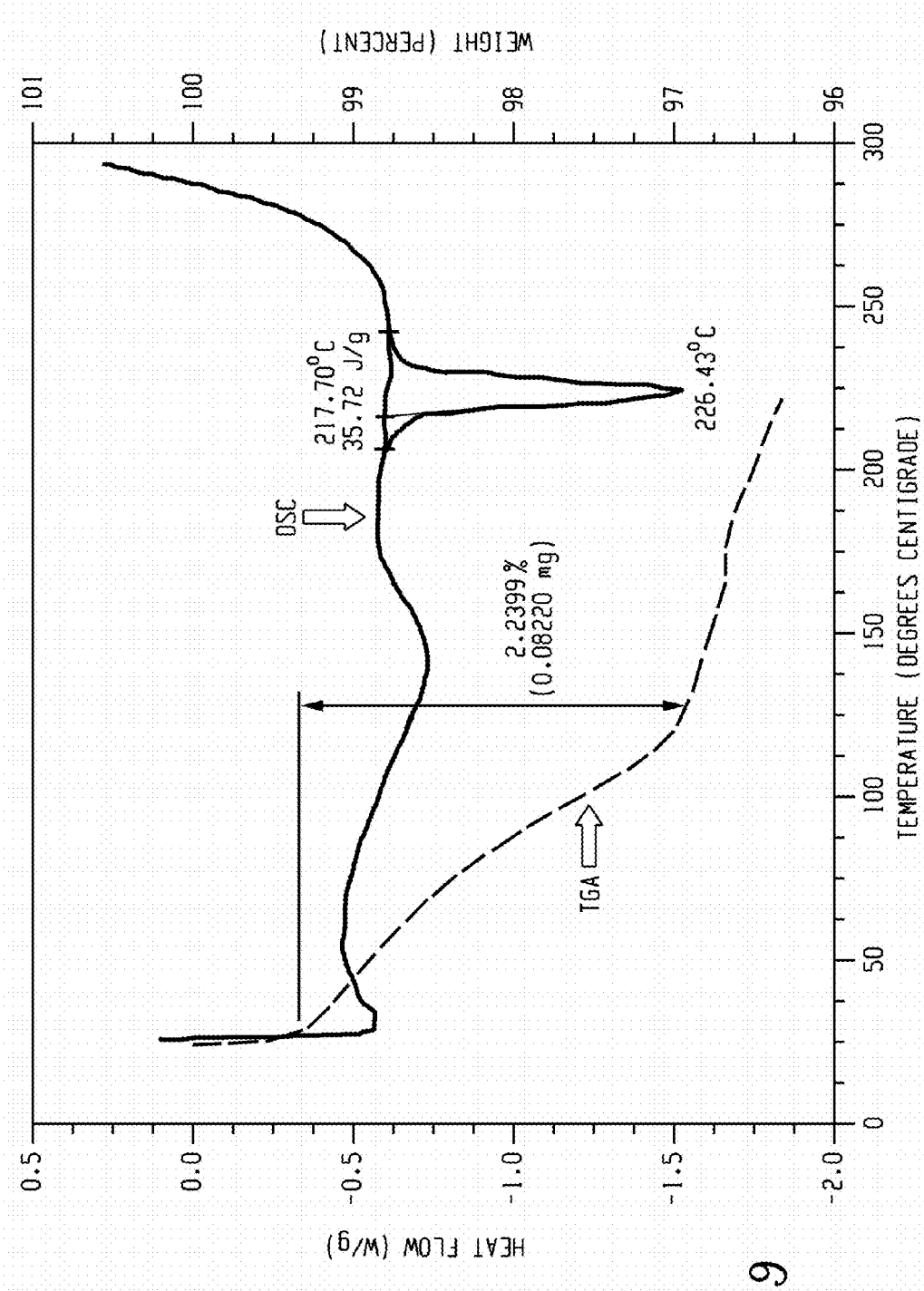
FIG. 9 is a graph of heat flow (Watts per gram) and weight (percent) versus temperature (° C.) showing the results of differential scanning calorimetry analysis/thermogravimetric analysis of the first Polymorph A sample.
Figure 10:
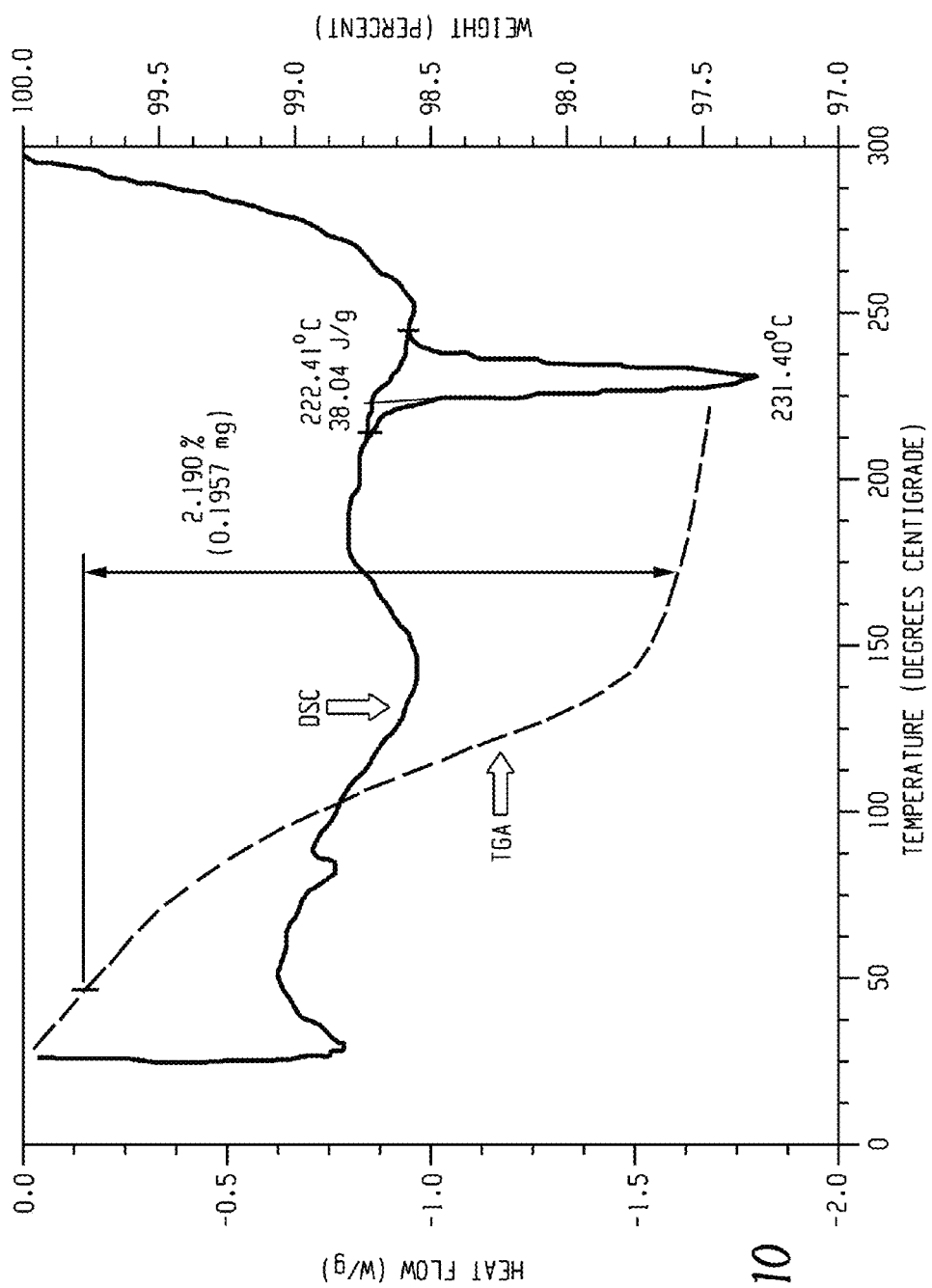
FIG. 10 is a graph of heat flow (Watts per gram) and weight (percent) versus temperature (° C.) showing the results of differential scanning calorimetry analysis/thermogravimetric analysis of the second Group A sample.

DSC data of Polymorph A shows a broad endotherm above 50° C. followed by a second sharp melting endotherm above 200° C. TGA data obtained on various batches of Polymorph A show weight loss between 1.9-2.3%. TGA-IR analysis of the evolved gases shows the presence of water indicating that Polymorph A is a hydrated form. Raman (FIG. 7), PXRD (FIG. 8), and DSC (FIG. 9) data are provided. Multiple batches of Polymorph A gave substantially identical analytical results.

Figure 2:
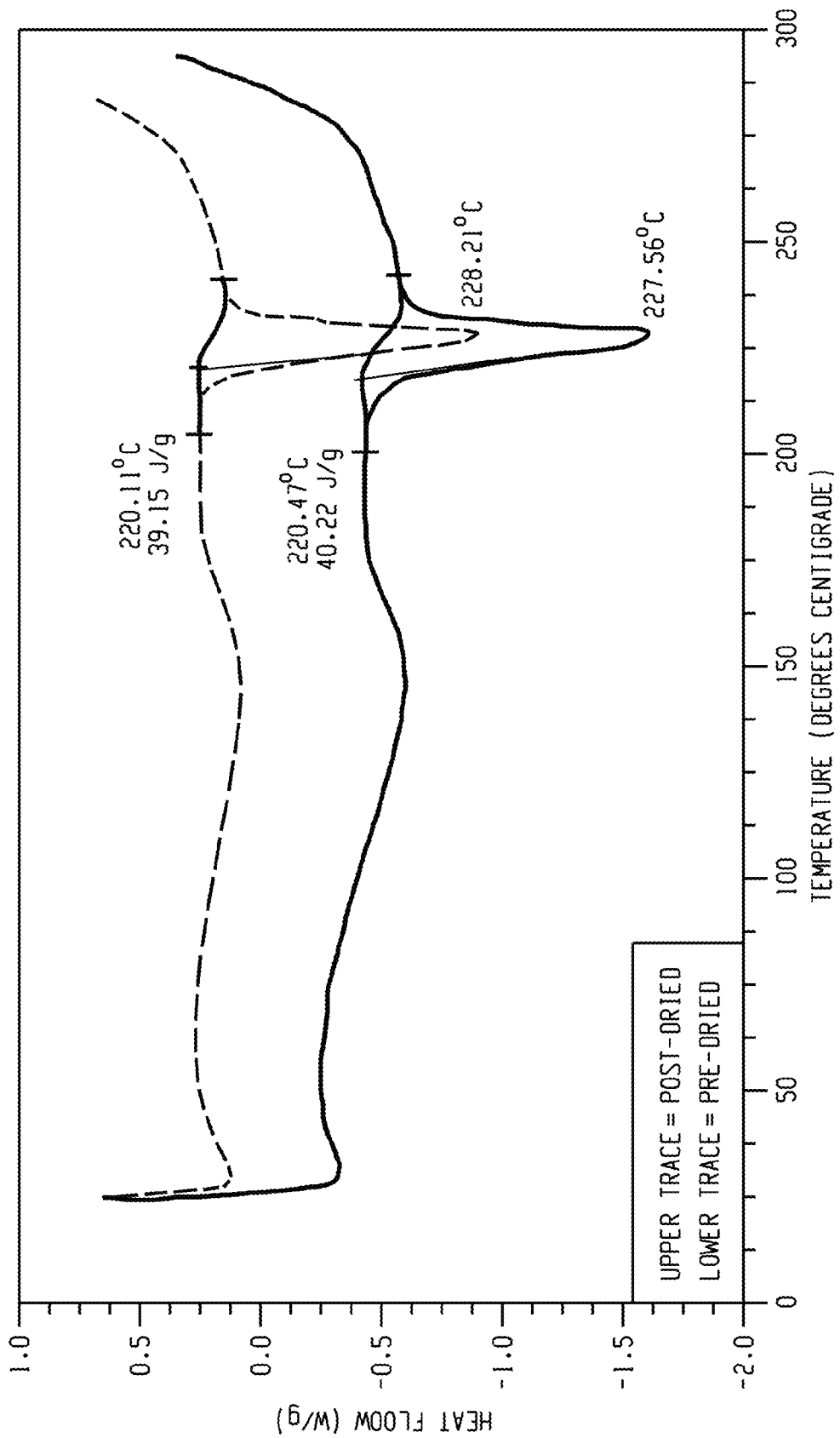
FIG. 2 is a graph of heat flow (Watts per gram) versus temperature (° C.) showing the results of differential scanning calorimetry overlay of a pre-dried (lower trace) and post-dried (upper trace) Polymorph A sample.
Figure 3:
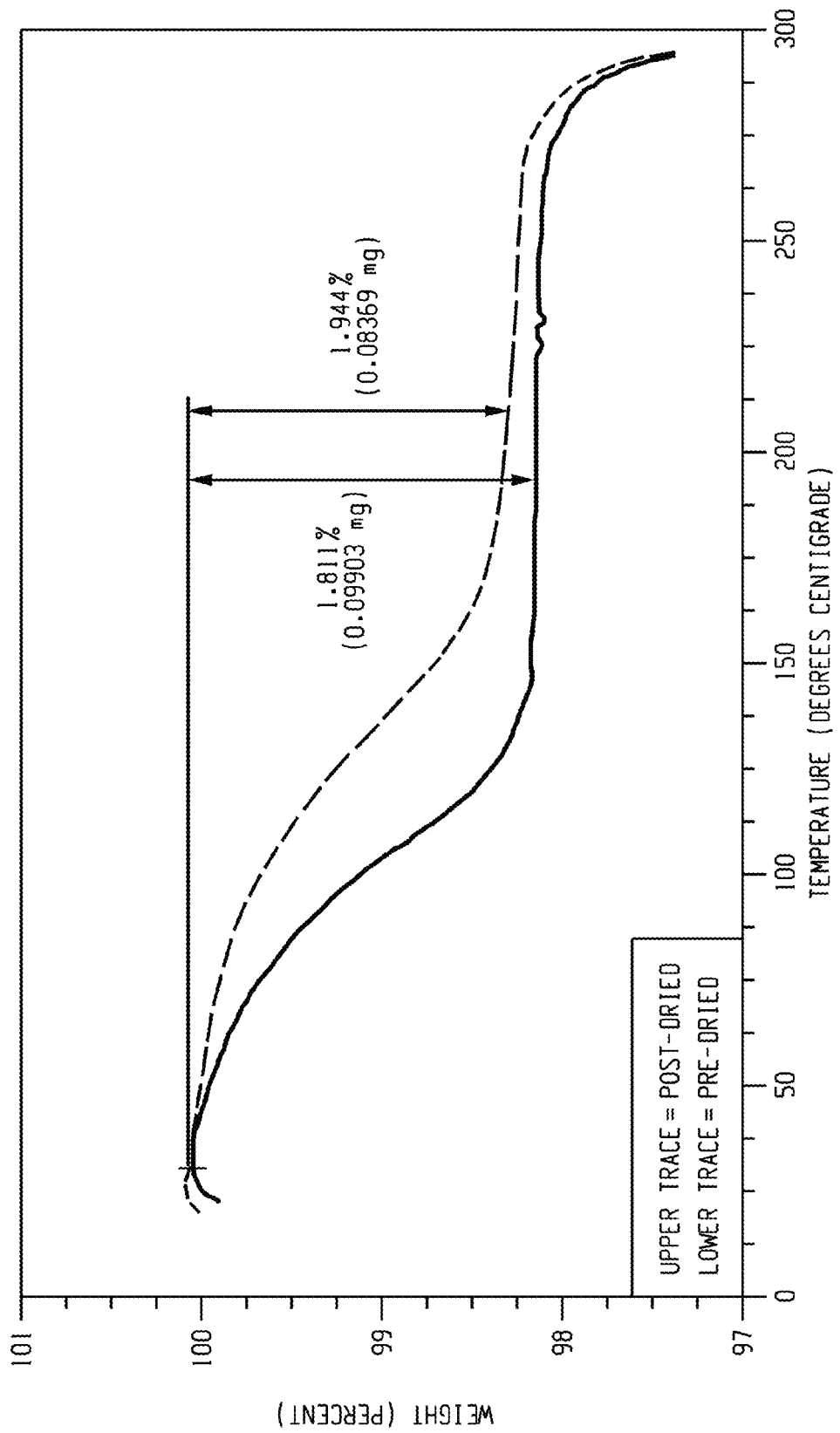
FIG. 3 is a graph of weight (percent) versus temperature (° C.) showing the results of thermogravimetric analysis of the Form A polymorph.

A sample of Polymorph A was dried in a vacuum oven at 55° C. overnight with a small flow of nitrogen. FIG. 1 is a graph showing the results of X-ray powder diffraction analysis of pre-dried (lower trace) and post-dried (upper trace) Polymorph A sample. FIG. 2 is a graph showing the results of differential scanning calorimetry overlay of a pre-dried (lower trace) and post-dried (upper trace) Polymorph A sample. FIG. 3 is a graph showing the results of thermogravimetric analysis of the Form A polymorph. PXRD analysis of the dried sample does not show any change in form or crystallinity Thermal analysis of the vacuum dried sample does not show any significant changes when compared to the air-dried sample.

Example 5

Polymorph B (Iso-Structural Solvates)

Figure 13:
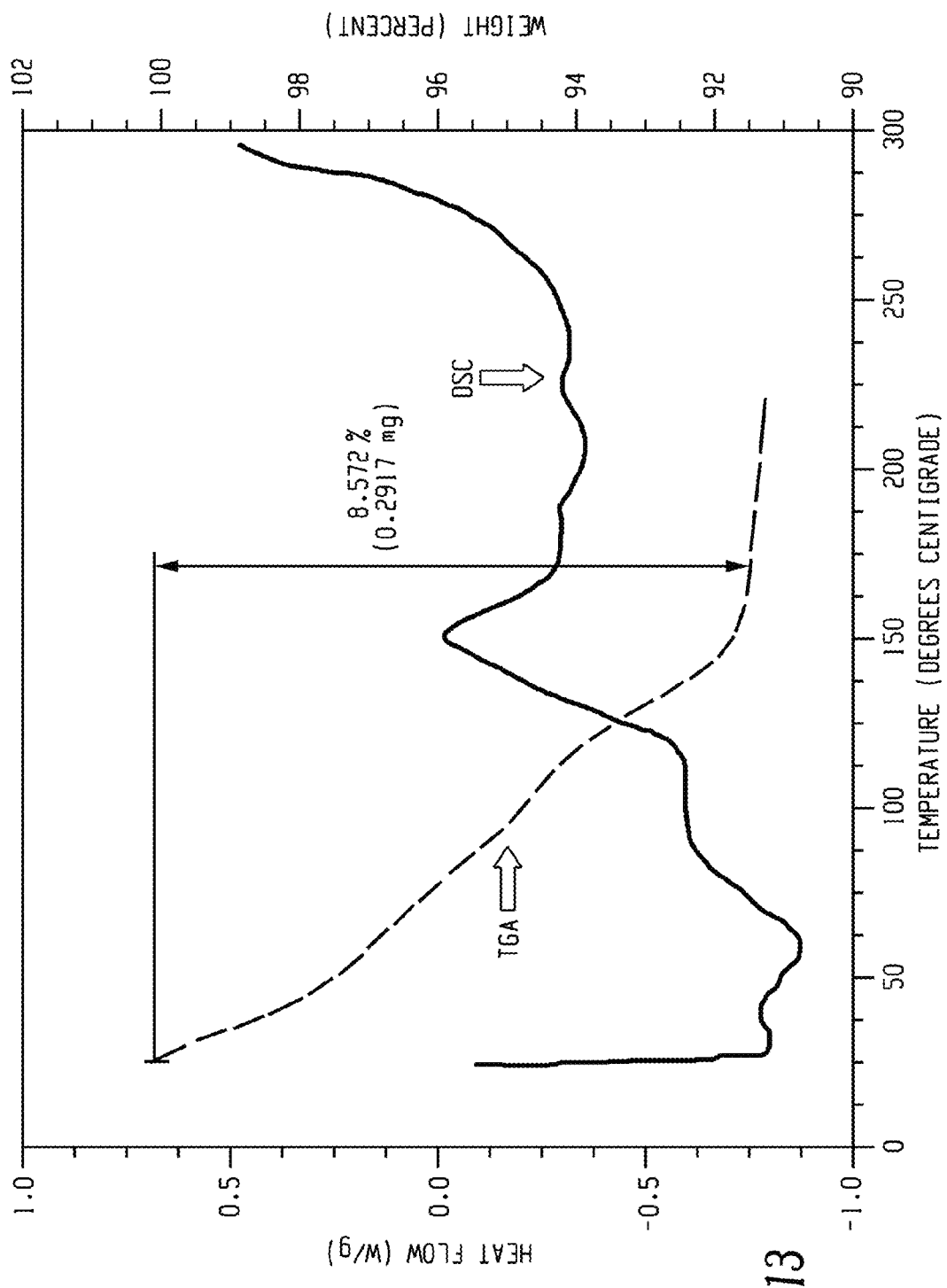
FIG. 13 is a graph of heat flow (Watts per gram) and weight (percent) versus temperature (° C.) showing the results of differential scanning calorimetry analysis/thermogravimetric analysis of the first Polymorph B sample.
Figure 14:
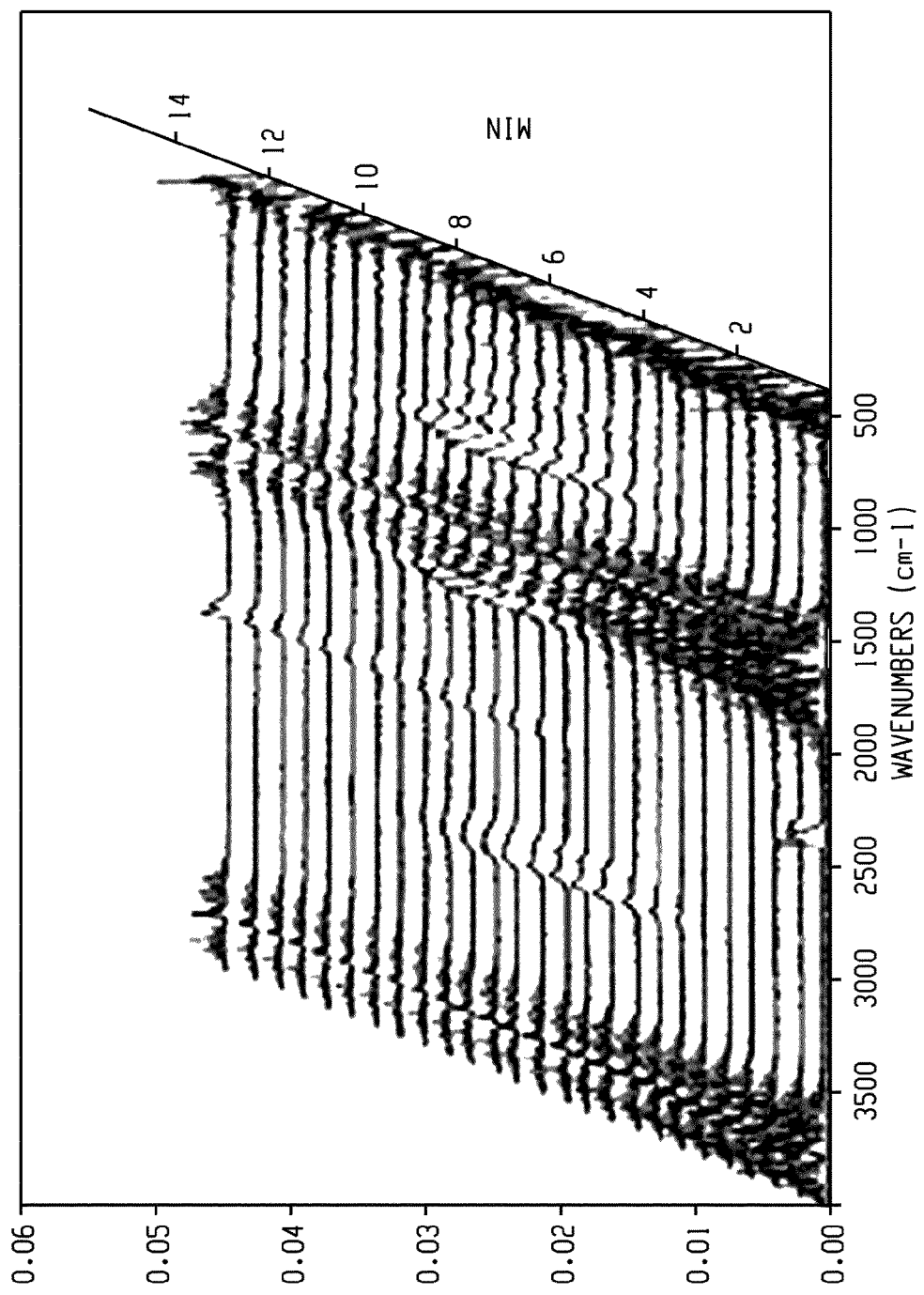
FIG. 14 is a graph of absorbance (arbitrary unit) versus wavelength (centimeter$^{-1}$) versus time (minute) showing the thermogravimetric/infra-red spectroscopy analysis waterfall plot of the first Polymorph B sample.

Polymorph B was isolated from two slurry-ripening experiments involving THF and 1,4-dioxane, and one evaporative crystallization experiment involving 1,4-dioxane:10% water as solvent. Raman and PXRD data of these samples reveal that these samples are similar to each other indicating that these samples are iso-structural. DSC data shows multiple and/or broad endotherms indicative of hydrated/solvated form. TGA-IR analysis of the evolved gases shows the presence of water and the respective solvent indicating that Polymorph B is a hydrate/solvate. Raman (FIG. 11), PXRD (FIG. 12), DSC (FIG. 13), and TGA-IR (FIG. 14) data are provided. Multiple batches of Polymorph B gave substantially identical analytical results.

Figure 4:
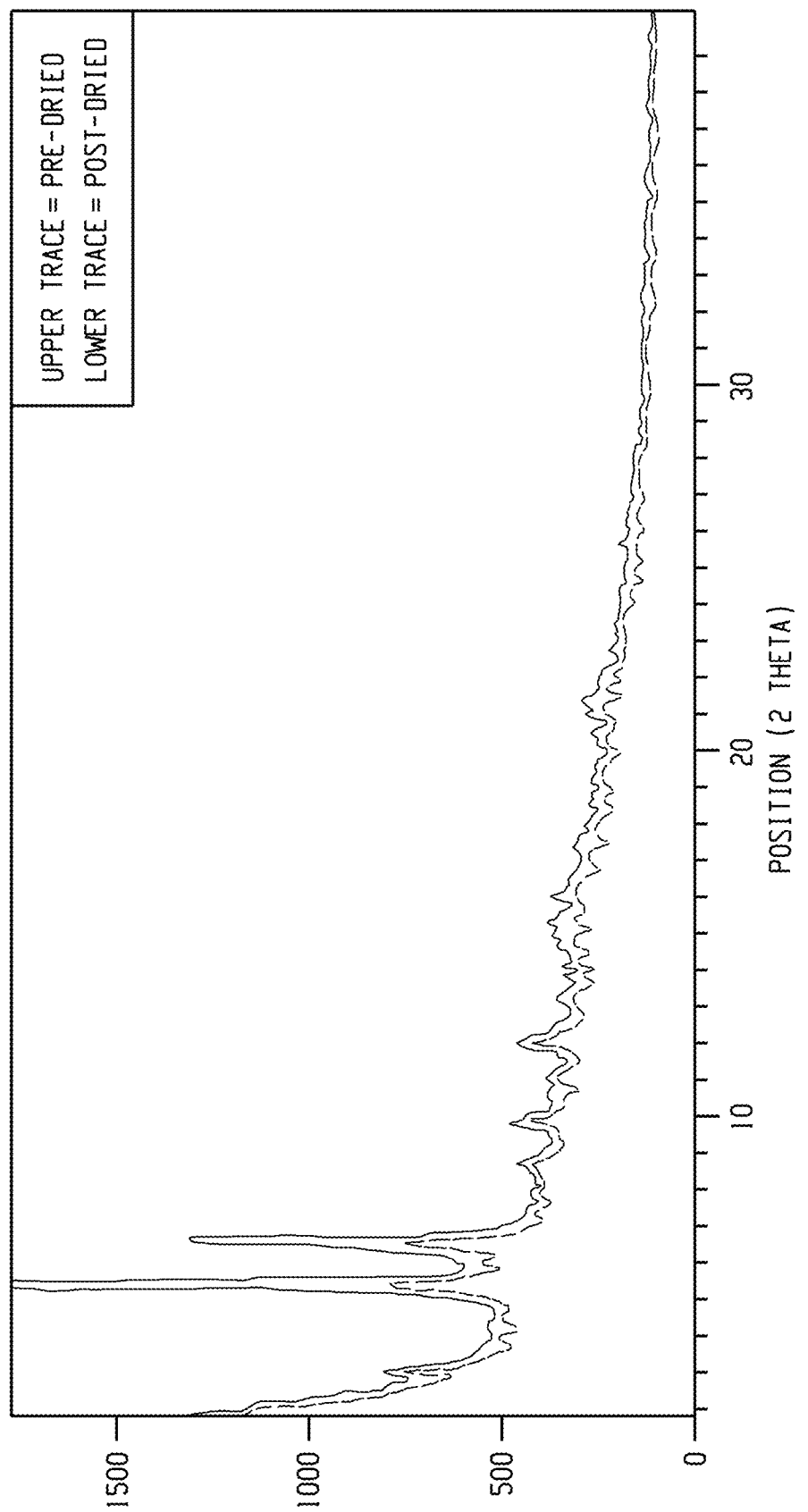
FIG. 4 is a graph of intensity (counts per second) versus scattering angle (degrees 2θ) showing the results of X-ray powder diffraction analysis of the first pre-dried (upper trace) and post-dried (lower trace) Polymorph B sample.
Figure 5:
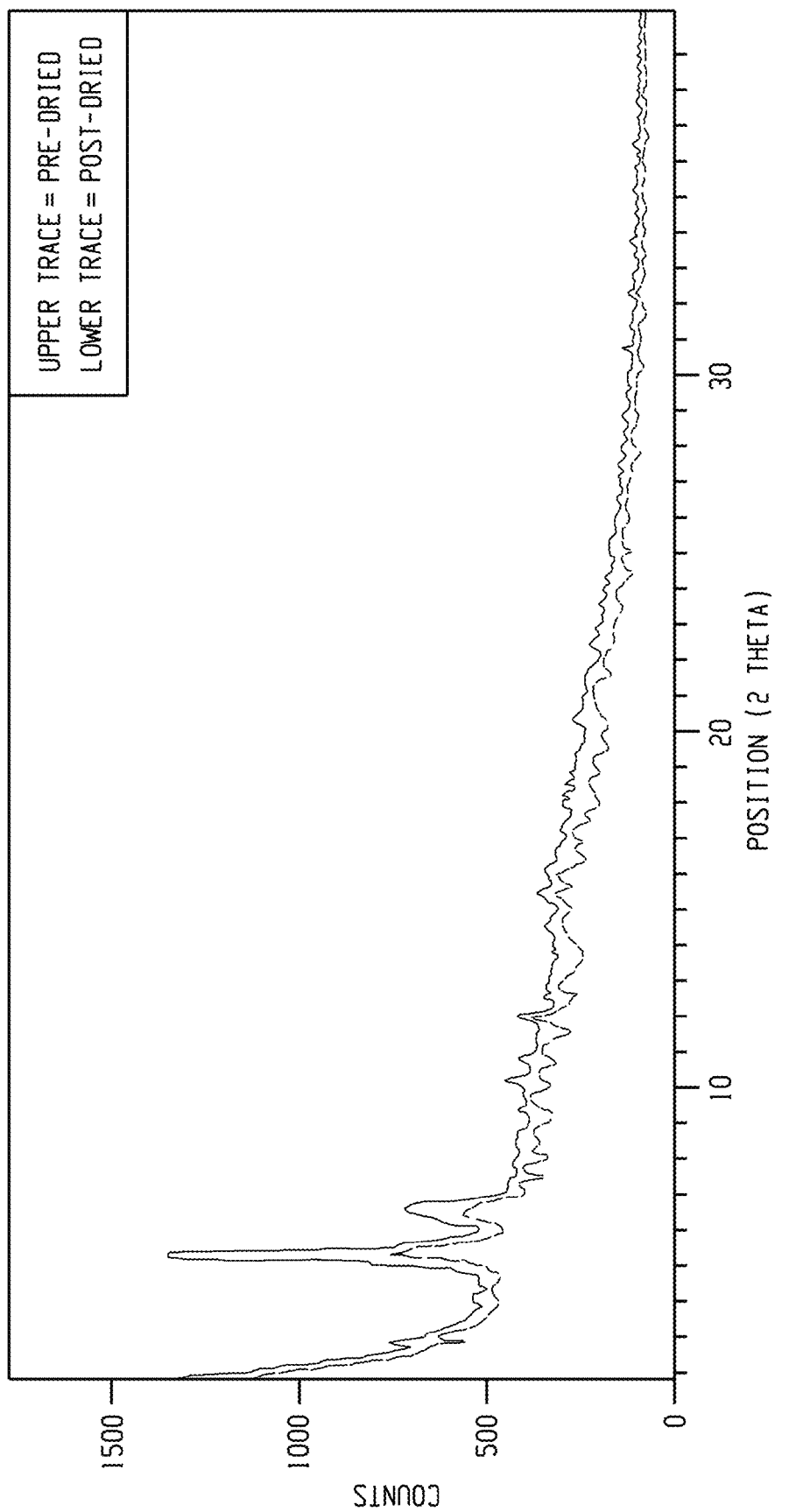
FIG. 5 is a graph of intensity (counts per second) versus scattering angle (degrees 2θ) showing the results of X-ray powder diffraction analysis of the second pre-dried (upper trace) and post-dried (lower trace) Polymorph B sample.

A small amount of Polymorph B was dried in a vacuum oven at 50° C. for 16 hours and the sample was re-analyzed by PXRD to observe if there were any form changes. The PXRD pattern (FIGS. 4 and 5) of the dried sample does not show any change in form but the peaks appear to be broader indicating that extended drying of the sample may lead to a loss of crystallinity and an increase in amorphous content.

Example 6

Polymorph C (1-Methoxy-2-Propanol Solvate)

Figure 16:
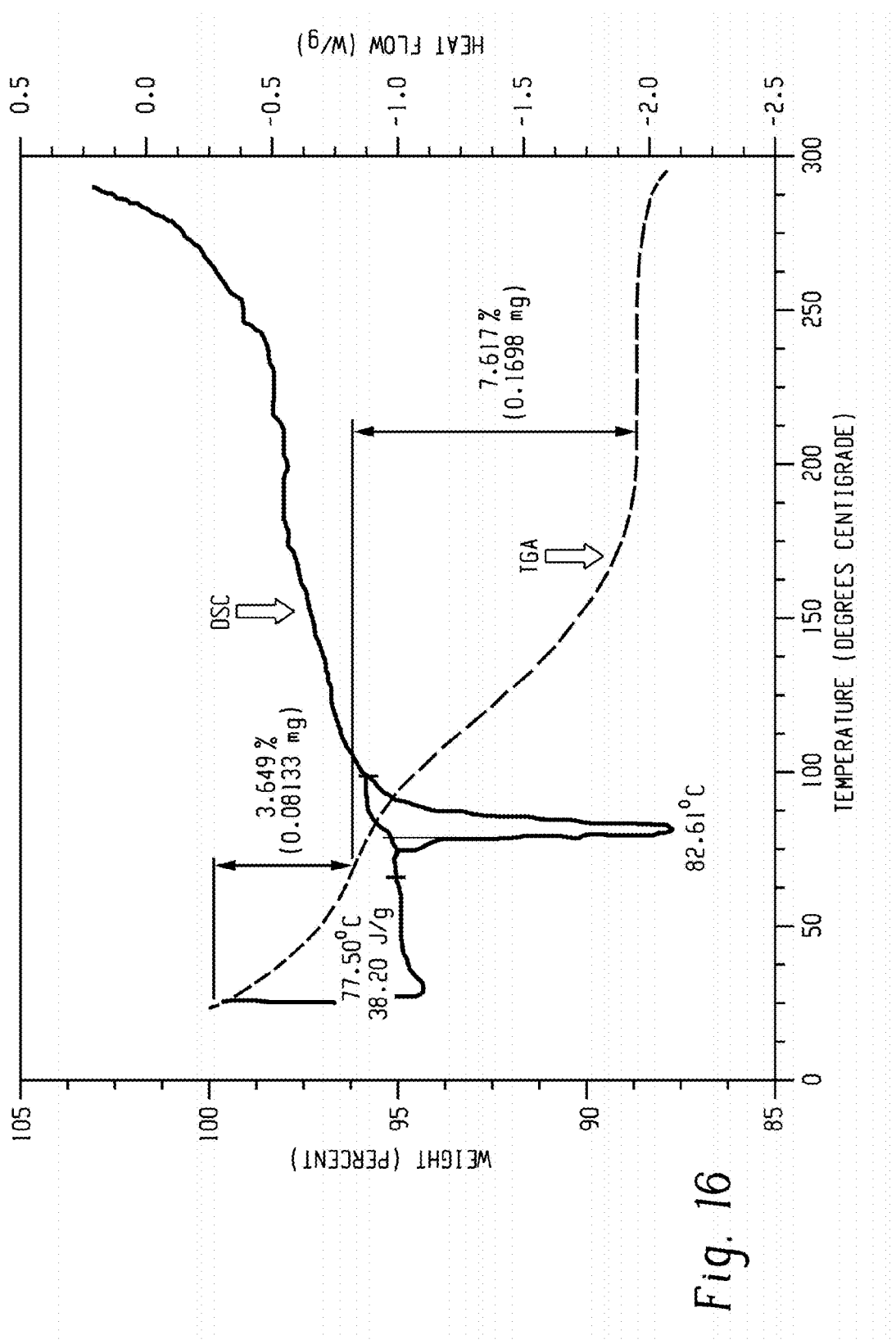
FIG. 16 is a graph of heat flow (Watts per gram) and weight (percent) versus temperature (° C.) showing the results of differential scanning calorimetry analysis/thermogravimetric analysis of the Polymorph C sample.
Figure 17:
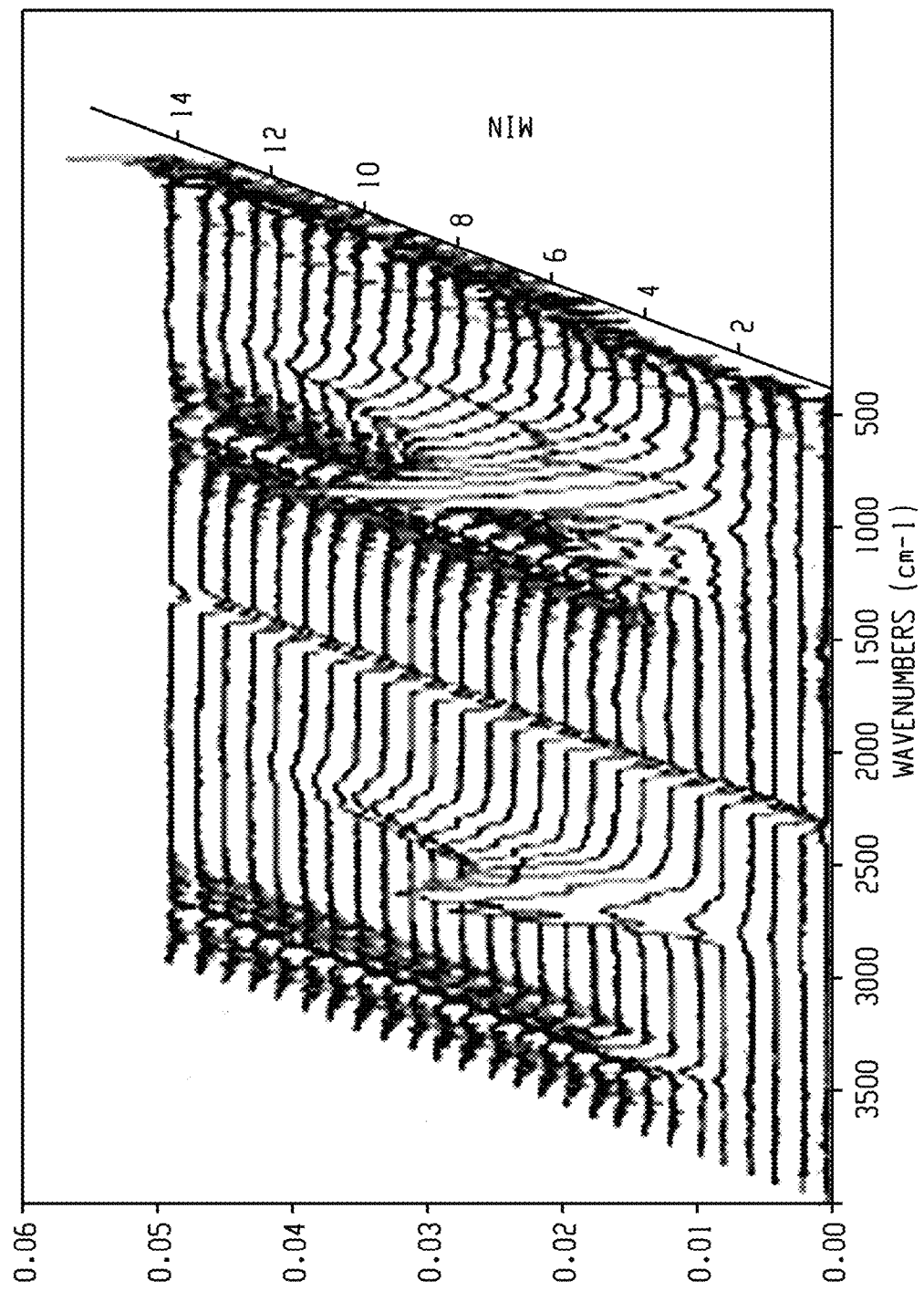
FIG. 17 is a graph of absorbance (arbitrary unit) versus wavelength (centimeter$^{-1}$) versus time (minute) showing the thermogravimetric/infra-red spectroscopy analysis waterfall plot of the Polymorph C sample.

Polymorph C was isolated from a cooling crystallization experiment involving 1-methoxy-2-propanol solvent. DSC data shows a primary endotherm at 82.6° C. TGA data shows ~11.3% weight loss between 25° C. and 200° C. TGA-IR analysis of the evolved gases shows the presence of solvent indicating that Polymorph C is a 1-methoxy-2-propanol solvate. PXRD (FIG. 15), DSC (FIG. 16), and TGA-IR (FIG. 17) data are provided.

Example 7

Polymorph D (Cyclohexannone Solvate)

Figure 19:
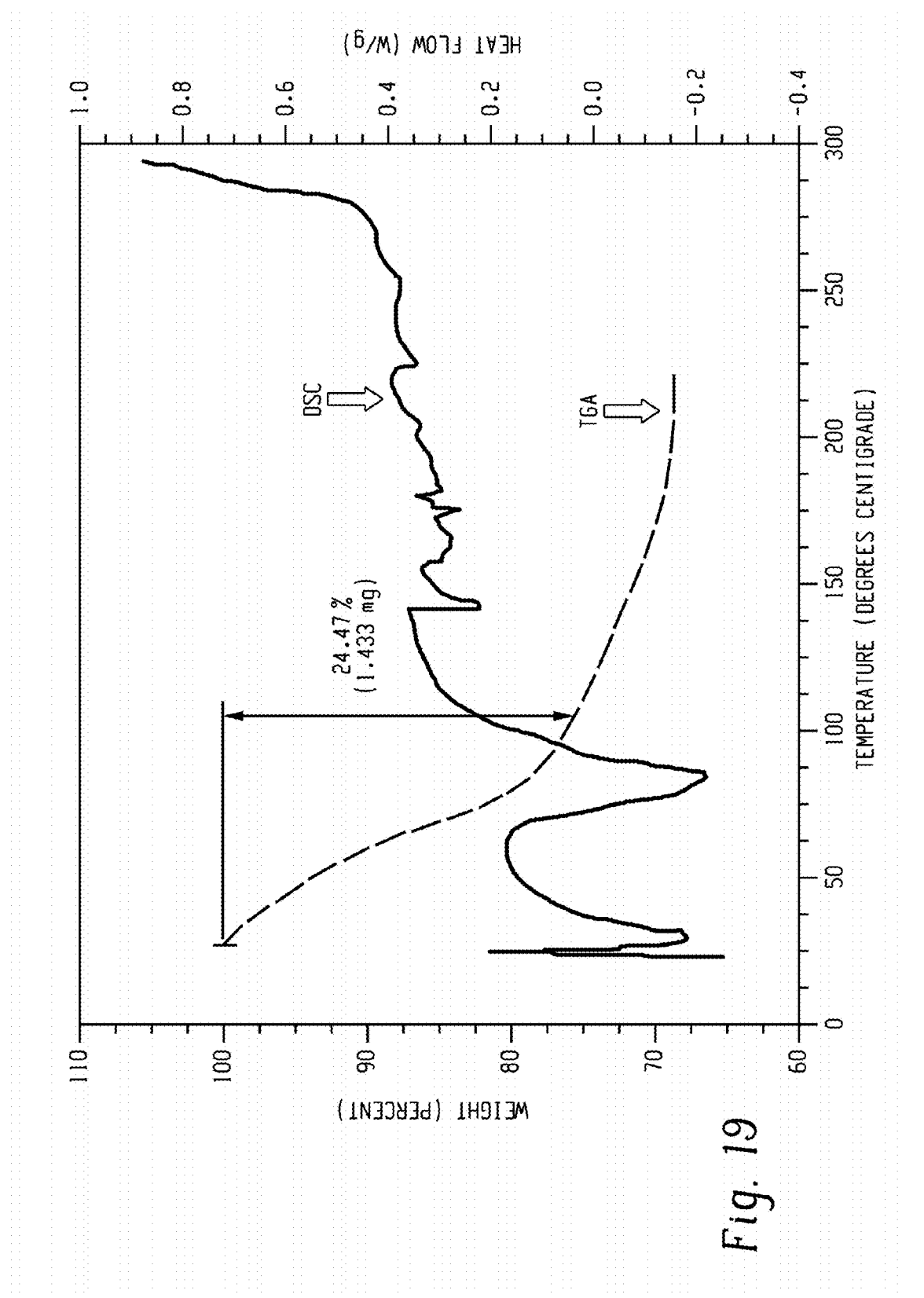
FIG. 19 is a graph of heat flow (Watts per gram) and weight (percent) versus temperature (° C.) showing the results of differential scanning calorimetry analysis/thermogravimetric analysis of the Polymorph D sample.
Figure 20:
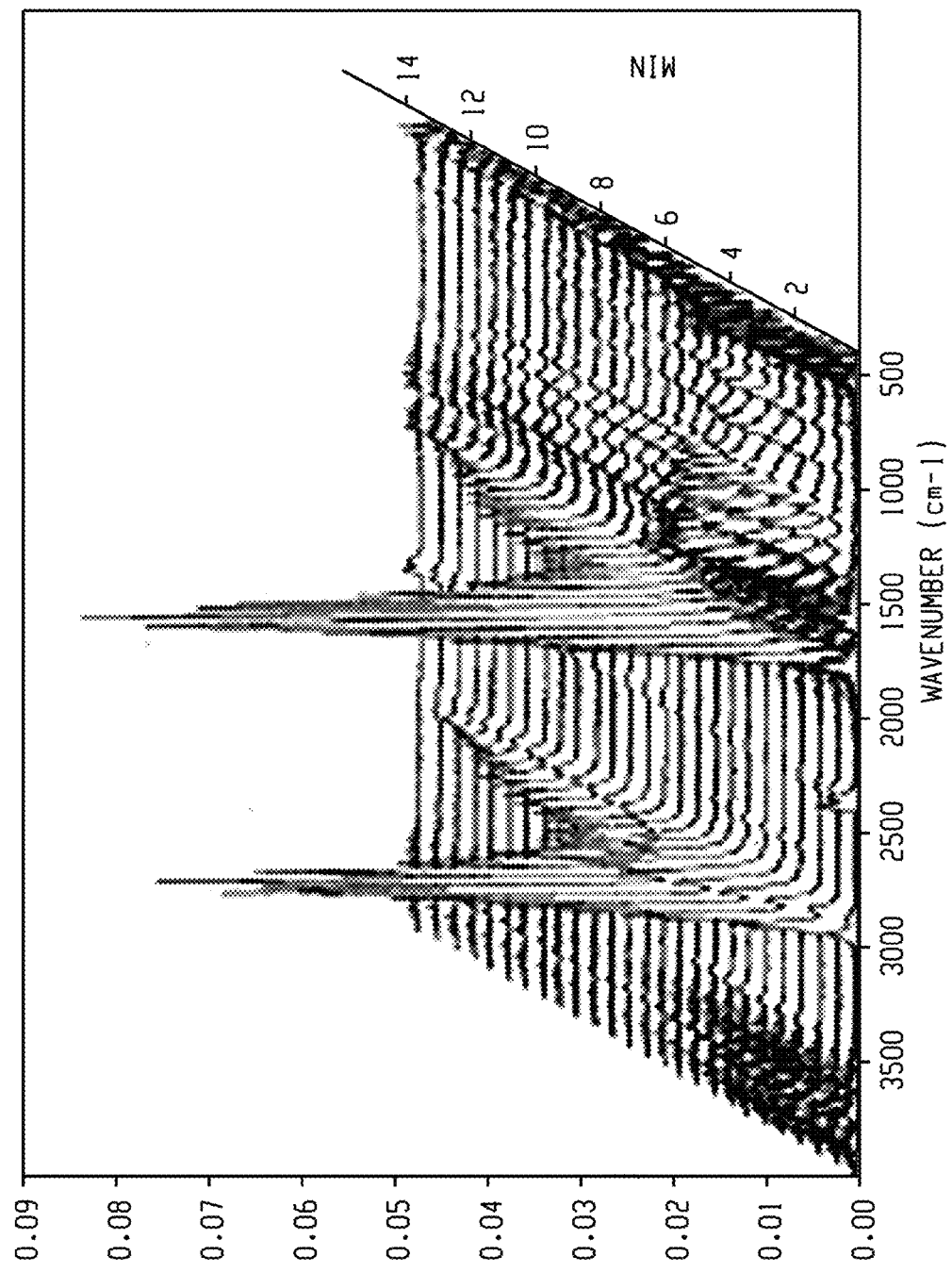
FIG. 20 is a graph of absorbance (arbitrary unit) versus wavelength (centimeter$^{-1}$) versus time (minute) showing the thermogravimetric/infra-red spectroscopy analysis waterfall plot of the Polymorph D sample.

Polymorph D was isolated from a vapor diffusion experiment involving cyclohexanone as solvent and pentane as an anti-solvent. DSC data shows multiple endotherms indicative of solvated form. TGA data shows ~24.5% weight loss below 105° C. TGA-IR analysis of the evolved gases shows the presence of water and cyclohexanone indicating that Polymorph D is a cyclohexanone solvate. PXRD (FIG. 18), DSC (FIG. 19), and TGA-IR (FIG. 20) data are provided.

Example 8

Polymorph E (DMSO Solvate)

Figure 22:
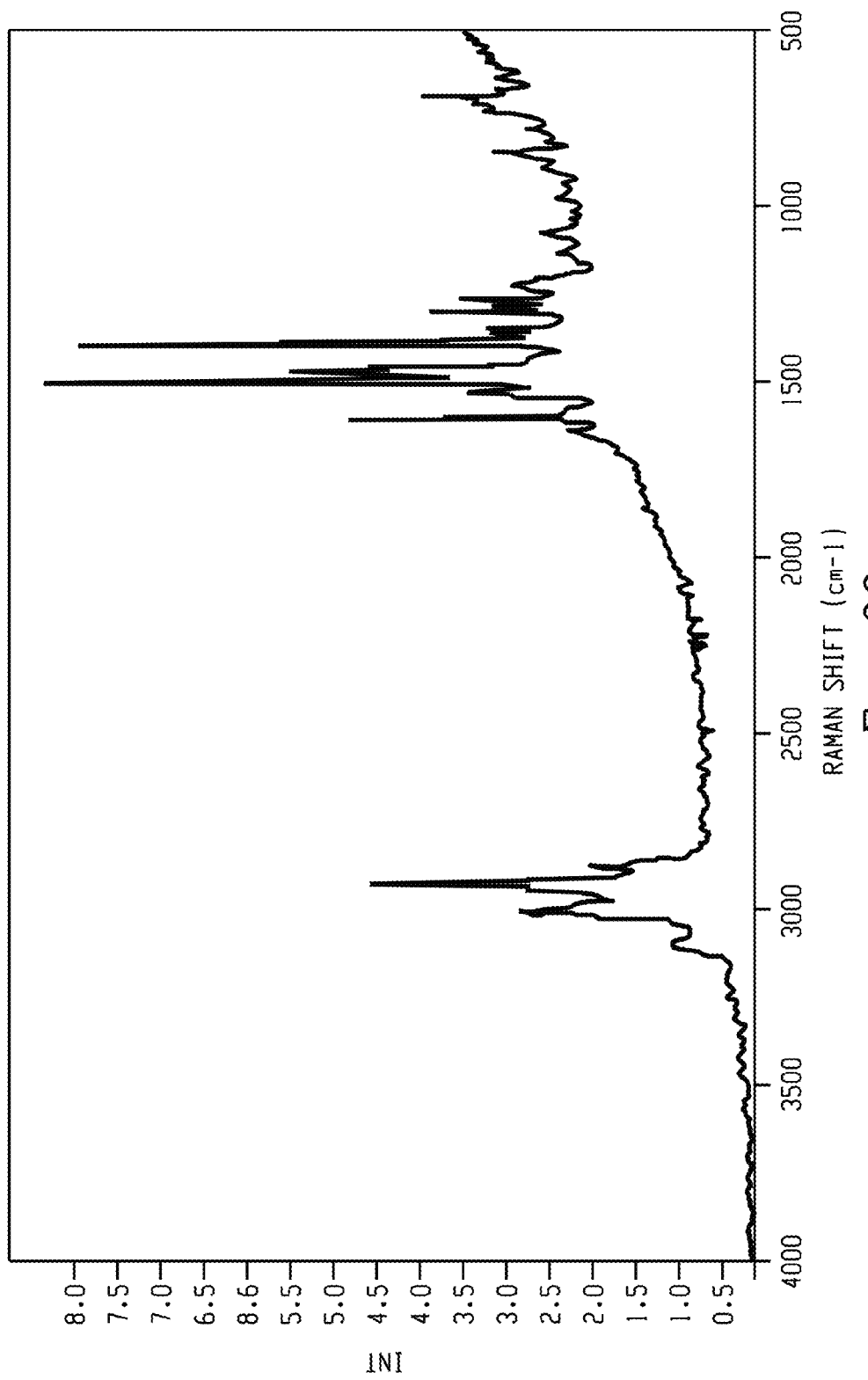
FIG. 22 is a graph of Raman intensity (arbitrary units) versus Raman shift (cm$^{-1}$) showing the FT-Raman spectrum of the Polymorph E sample.
Figure 23:
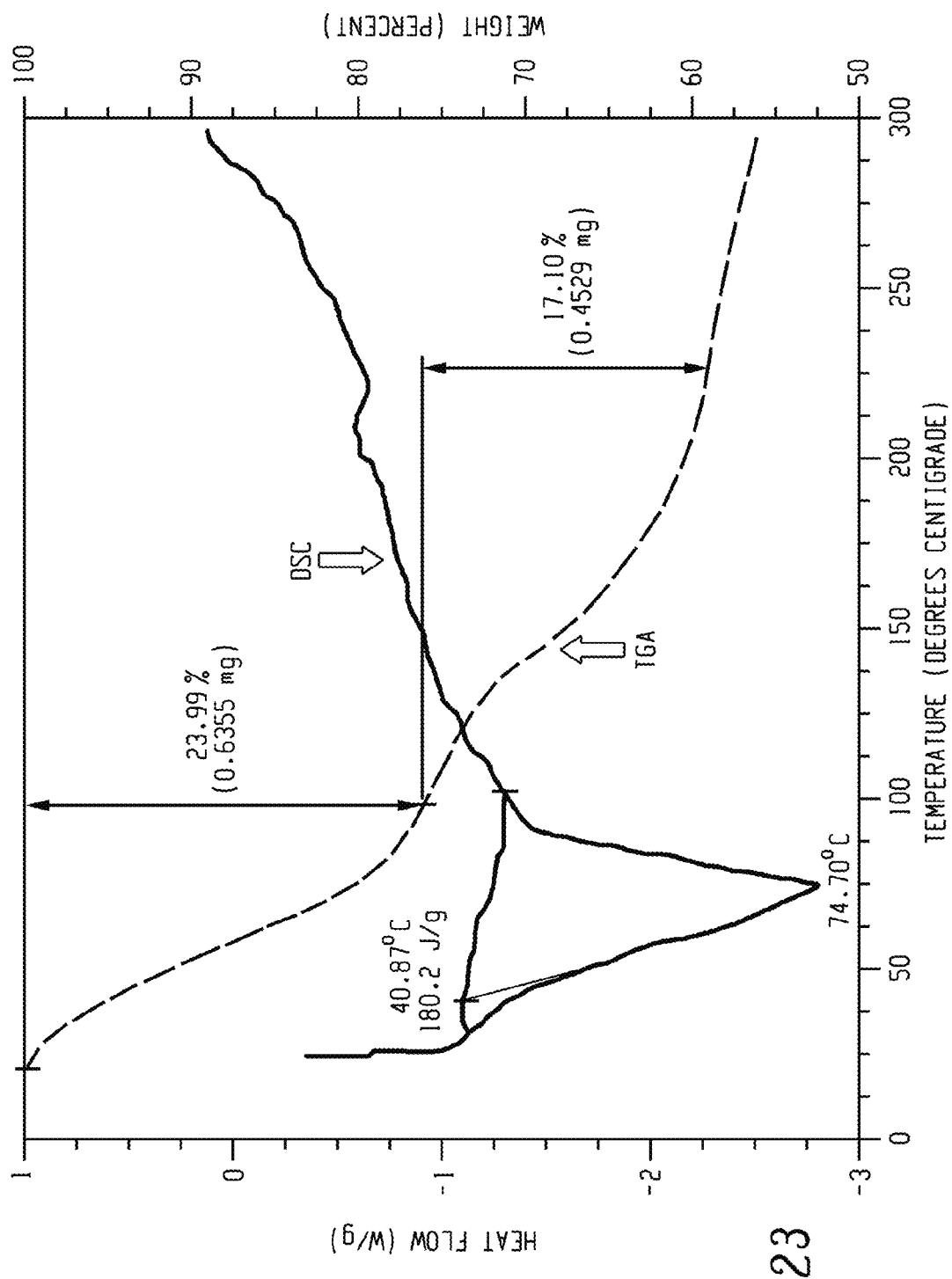
FIG. 23 is a graph of heat flow (Watts per gram) and weight (percent) versus temperature (° C.) showing the results of differential scanning calorimetry analysis/thermogravimetric analysis of the Polymorph E sample.

Polymorph E was isolated from a evaporative crystallization experiment involving DMSO as solvent. DSC data shows a broad endotherm below 100° C. indicative of a solvated form. The sample was found to be slightly wet. TGA data shows ~22.9% weight loss below 100° C. Raman (FIG. 22), PXRD (FIG. 21), and DSC/TGA (FIG. 23) data are provided.

Example 9

Polymorph F (Water/IPA Solvate)

Figure 25:
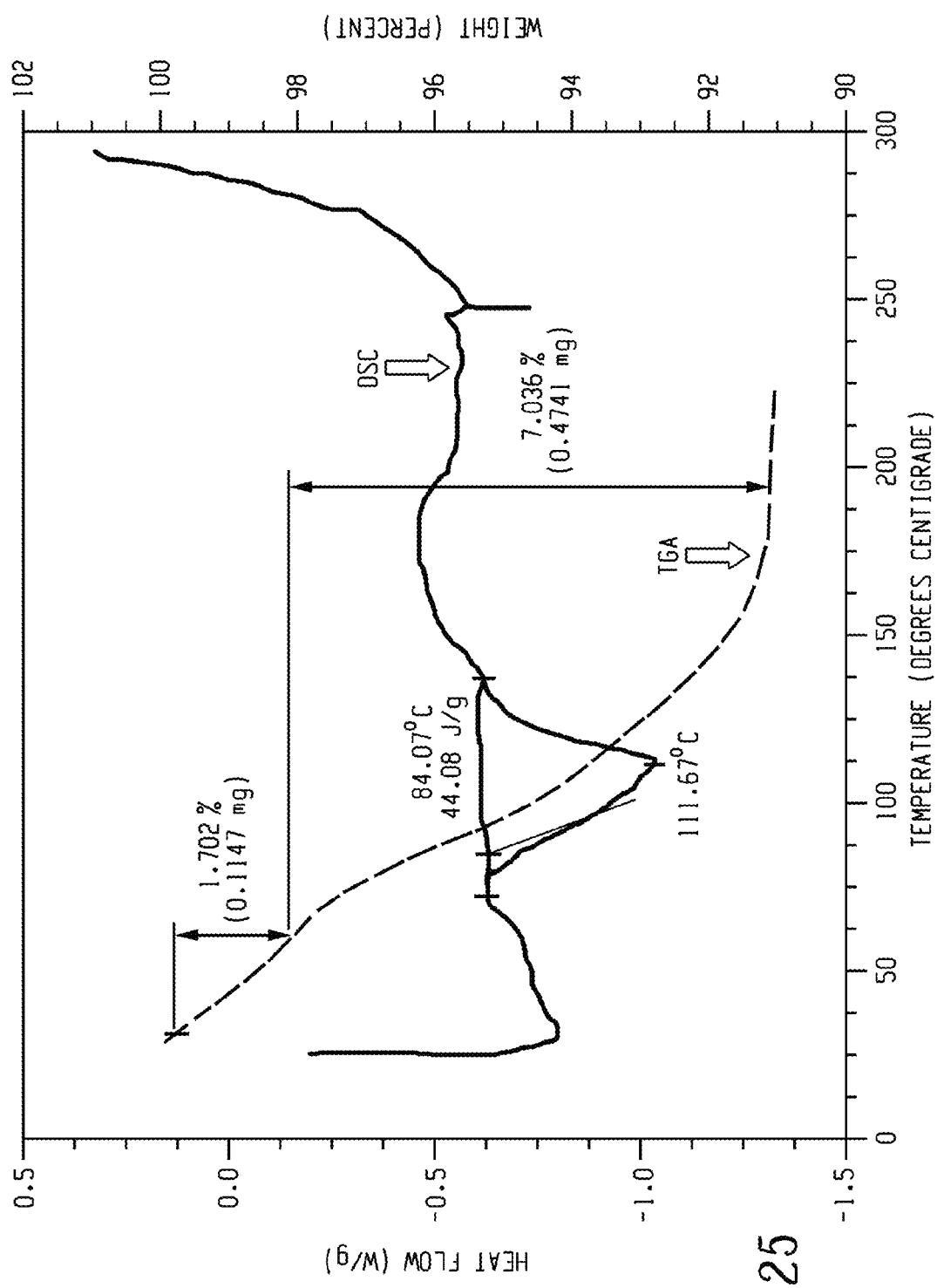
FIG. 25 is a graph of heat flow (Watts per gram) and weight (percent) versus temperature (° C.) showing the results of differential scanning calorimetry analysis/thermogravimetric analysis of the Polymorph F sample.
Figure 26:
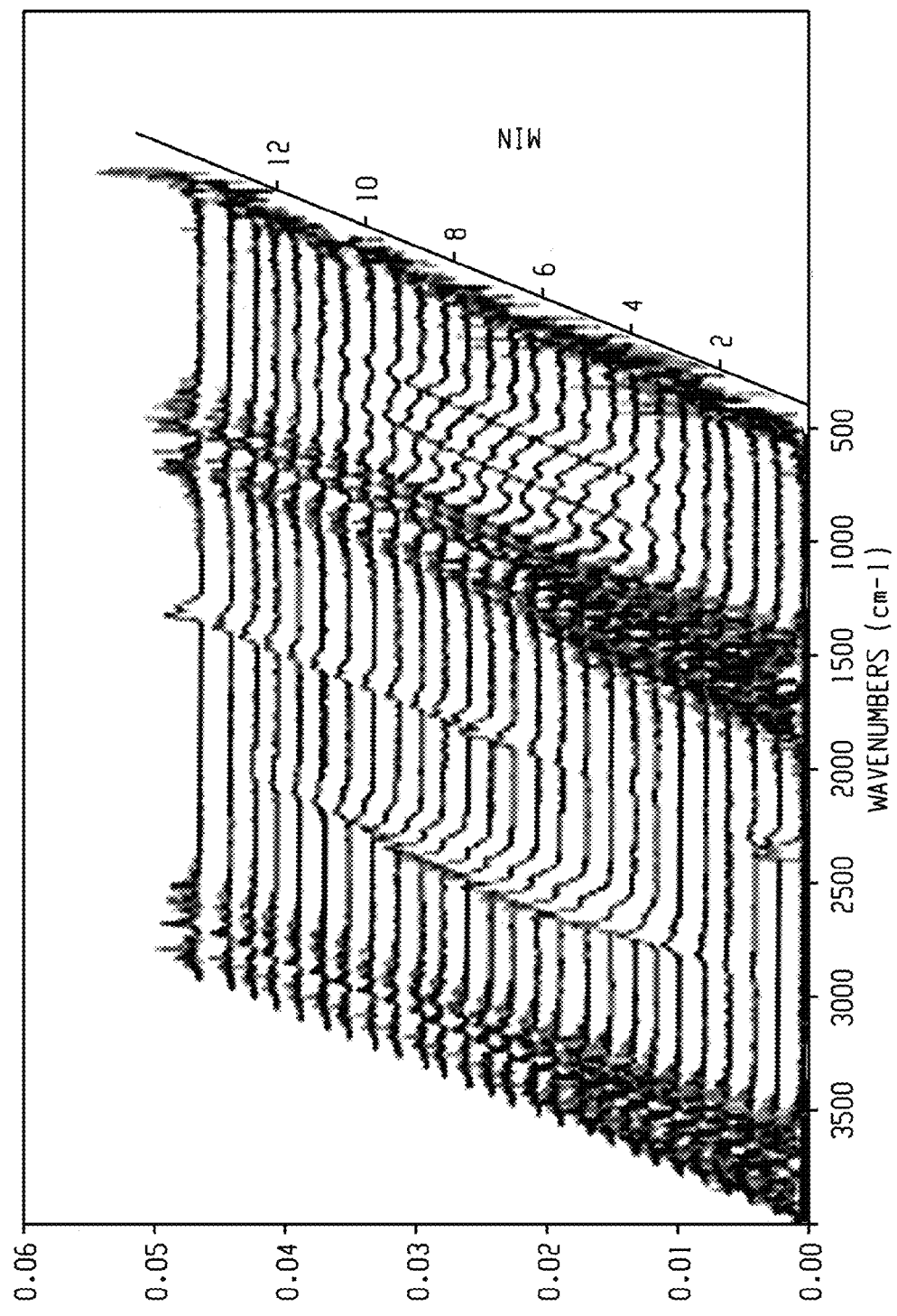
FIG. 26 is a graph of absorbance (arbitrary unit) versus wavelength (centimeter$^{-1}$) versus time (minute) showing the thermogravimetric/infra-red spectroscopy analysis waterfall plot of the Polymorph F sample.

PXRD pattern of Polymorph F shows the material is crystalline but shows slightly broader peaks when compared to Batch ACH-0142684-21. DSC data shows a primary endotherm at 111.7° C. TGA data shows ~8.8% weight loss below 200° C. TGA-IR analysis of evolved gases shows the presence of water and IPA indicating that this batch is a water/IPA solvate. PXRD (FIG. 24), DSC/TGA (FIG. 25), and TGA-IR (FIG. 26) data are provided.

Example 10

Polymorph G (Non-Solvated Form)

Figure 28:
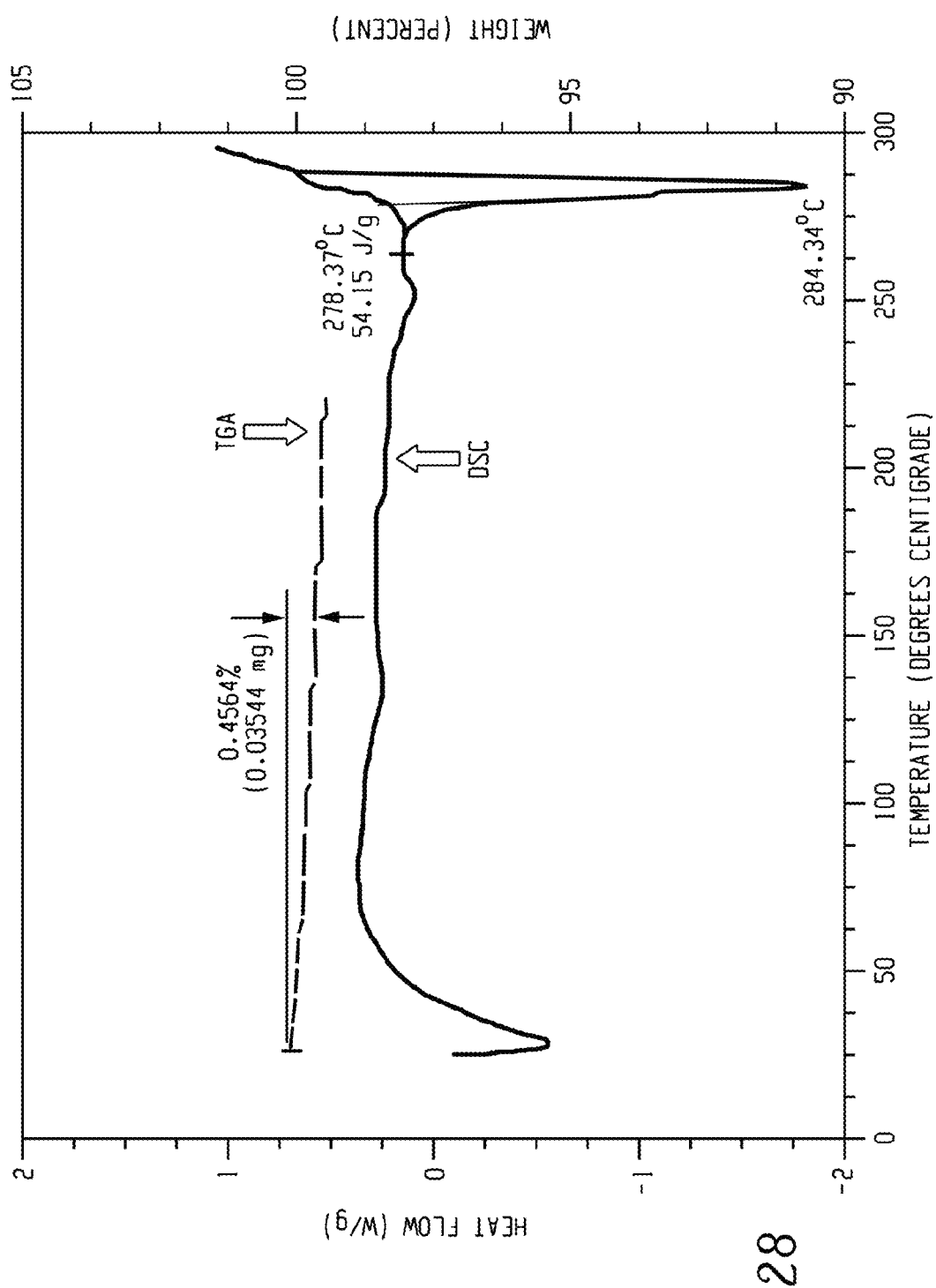
FIG. 28 is a graph of heat flow (Watts per gram) and weight (percent) versus temperature (° C.) showing the results of differential scanning calorimetry analysis/thermogravimetric analysis of the Polymorph G sample.
Figure 29:
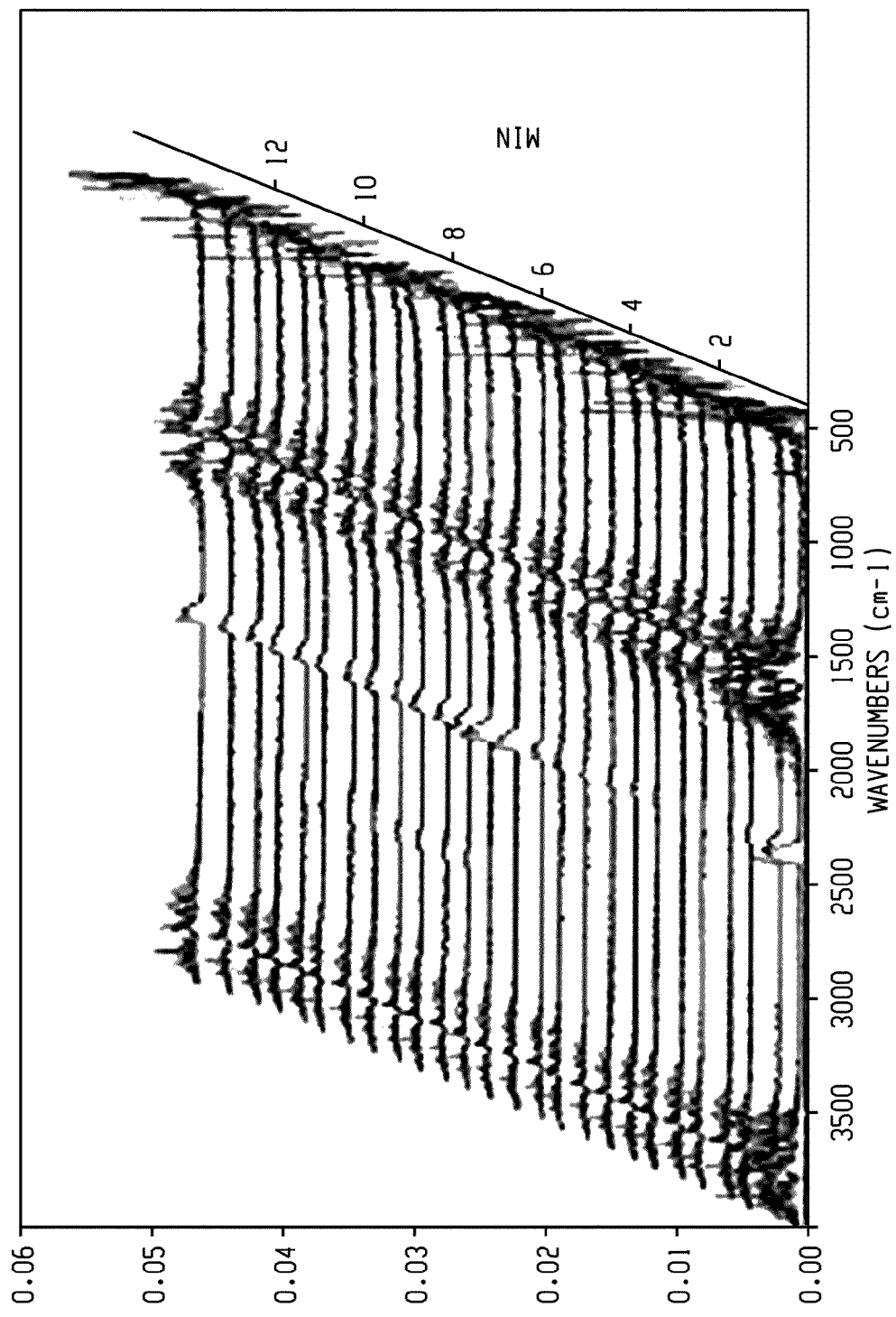
FIG. 29 is a graph of absorbance (arbitrary unit) versus wavelength (centimeter$^{-1}$) versus time (minute) showing the thermogravimetric/infra-red spectroscopy analysis waterfall plot of the Polymorph G sample.

The PXRD pattern of Polymorph G shows the material is crystalline. DSC data shows a primary endotherm at 284.3° C. TGA data shows less than 0.5% weight loss below 150° C. indicating that this batch is a non-solvated form. PXRD (FIG. 27), DSC/TGA (FIG. 28), and TGA-IR (FIG. 29) data are provided.

Example 11

Polymorph H

The Polymorph H form was prepared by dissolving the sodium salt of ACH-0142684 in ethanol and drying in vacuum oven at 40° C. PXRD pattern of Polymorph H shows the material is crystalline (FIG. 30).

Example 12

Polymorph I

Figure 32:
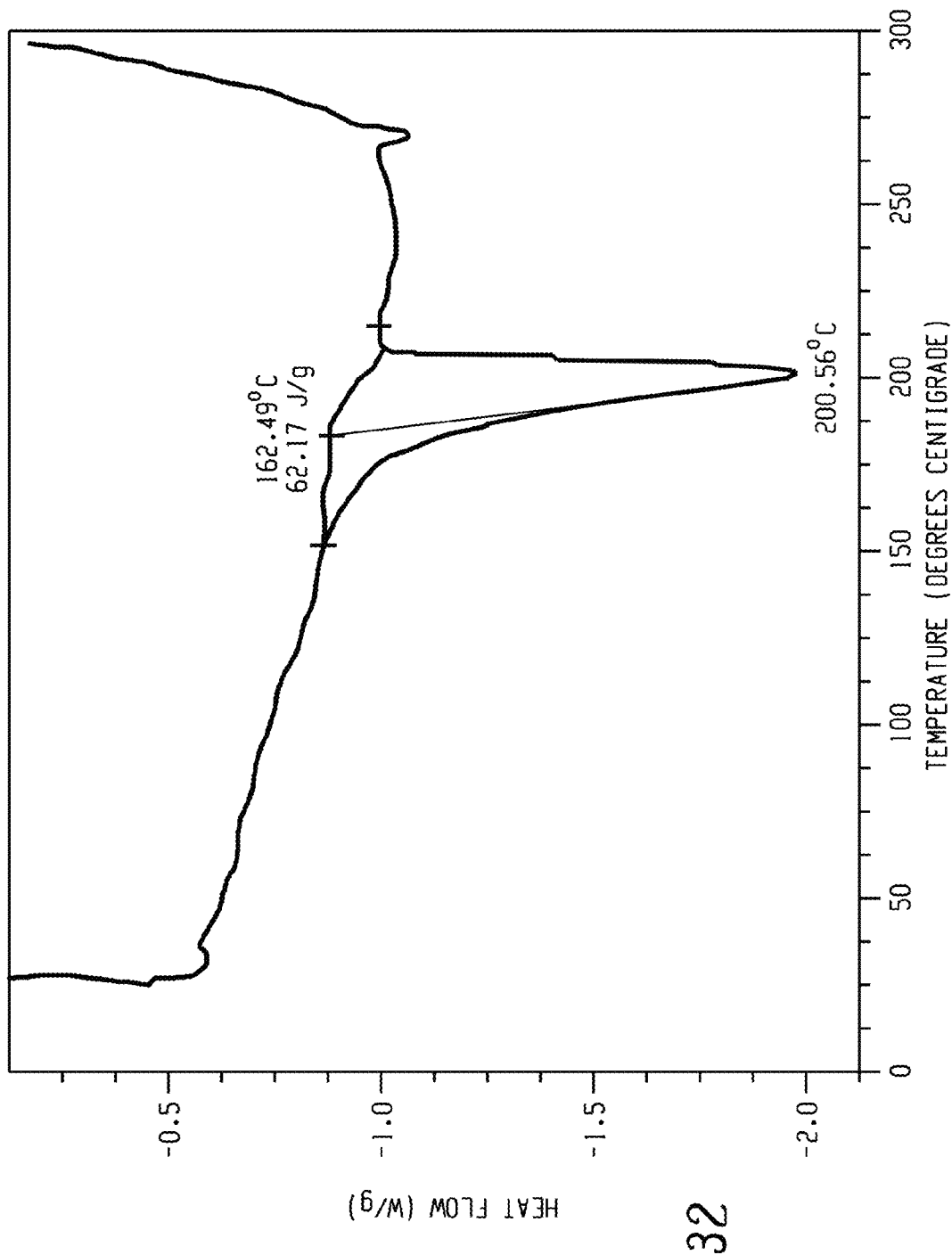
FIG. 32 is a graph of heat flow (Watts per gram) versus temperature (° C.) showing the results of differential scanning calorimetry of the Polymorph I sample.

The PXRD pattern of Polymorph I shows the material is crystalline (FIG. 31). DSC data shows a primary endotherm of 200.9° C. PXRD (FIG. 31), DSC (FIG. 32), and Raman (FIG. 33) are provided.

Form I was prepared by refluxing a suspension of amorphous ACH-0142684 in IPA [1:12 weight to volume] and the solid collected by filtration after cooling.

Example 13

Competitive Ripening Study

Figure 6:
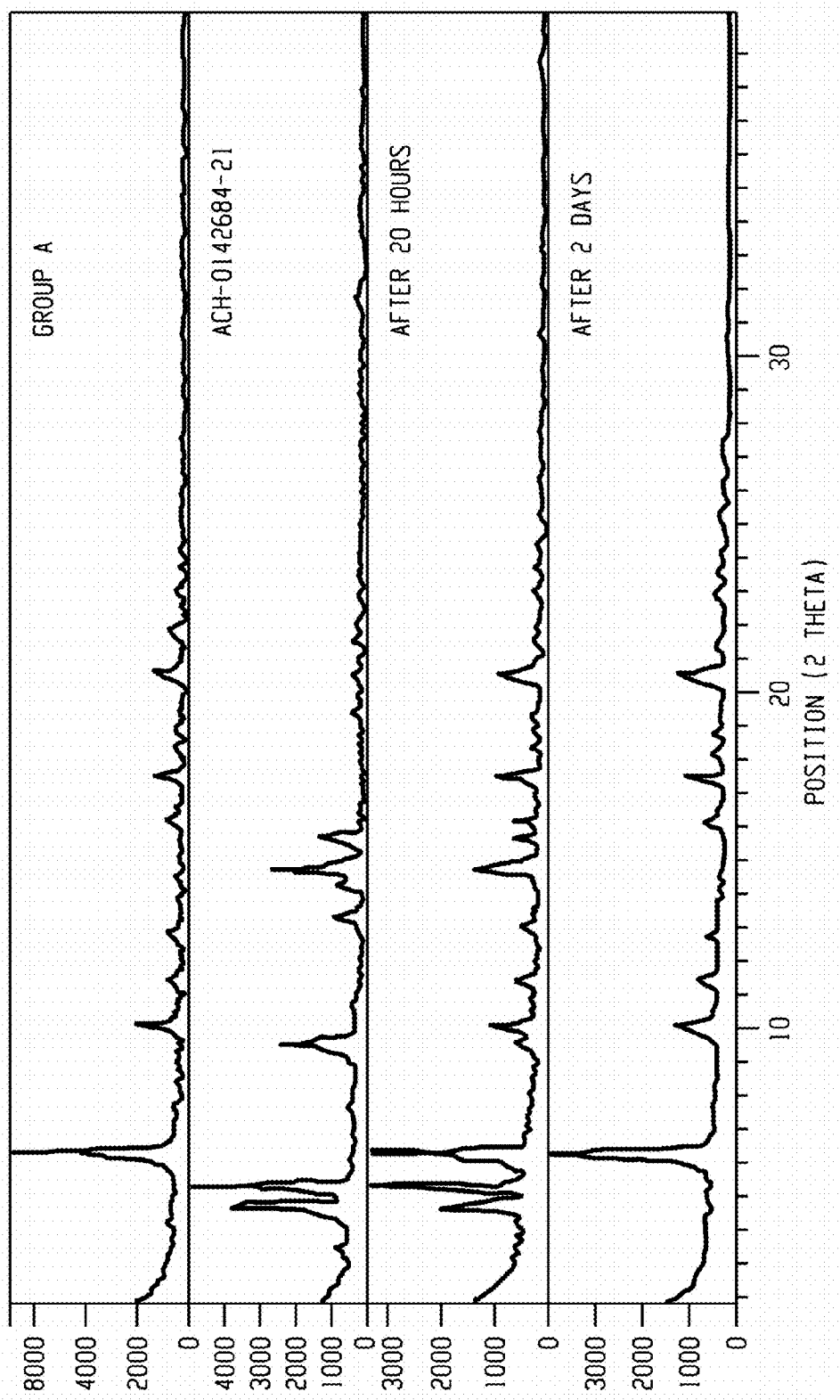
FIG. 6 is a graph of intensity (counts per second) versus scattering angle (degrees 2θ) showing a competitive ripening study and comparison of the results of X-ray powder diffraction analysis of Group A and Group G samples.

A competitive ripening study was conducted between Polymorphs A and G at room temperature to determine their relative stabilities. Approximately 5 mg of Polymorphs A and G were added to a 2-mL HPLC vial containing 0.5 mL of 2-propanol. The suspension was stirred at room temperature for two days. Aliquots of the slurry were filtered after 20 and 48 hours. The isolated solids were analyzed by PXRD to determine any form conversion. PXRD analysis (FIG. 6) indicates that the sample isolated after 20 hours were a mixture of the two forms while the sample isolated after 48 hours shows predominantly Polymorph A indicating that this form is the more stable form at room temperature.

Example 14

Synthesis of ACH-0142684 Sodium Salt

Step 1. Synthesis of Intermediate Compound 30

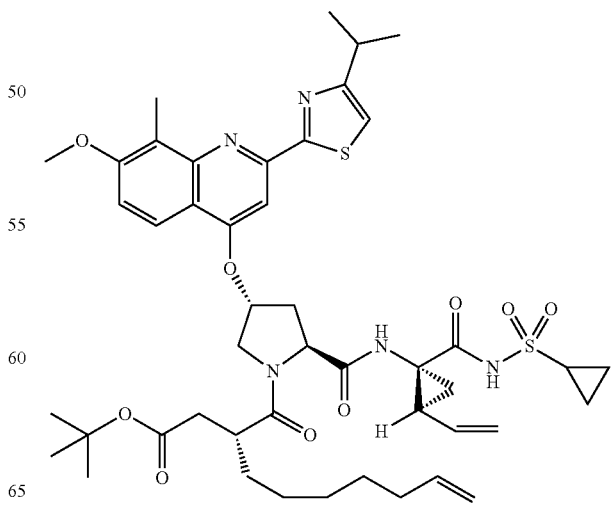

30

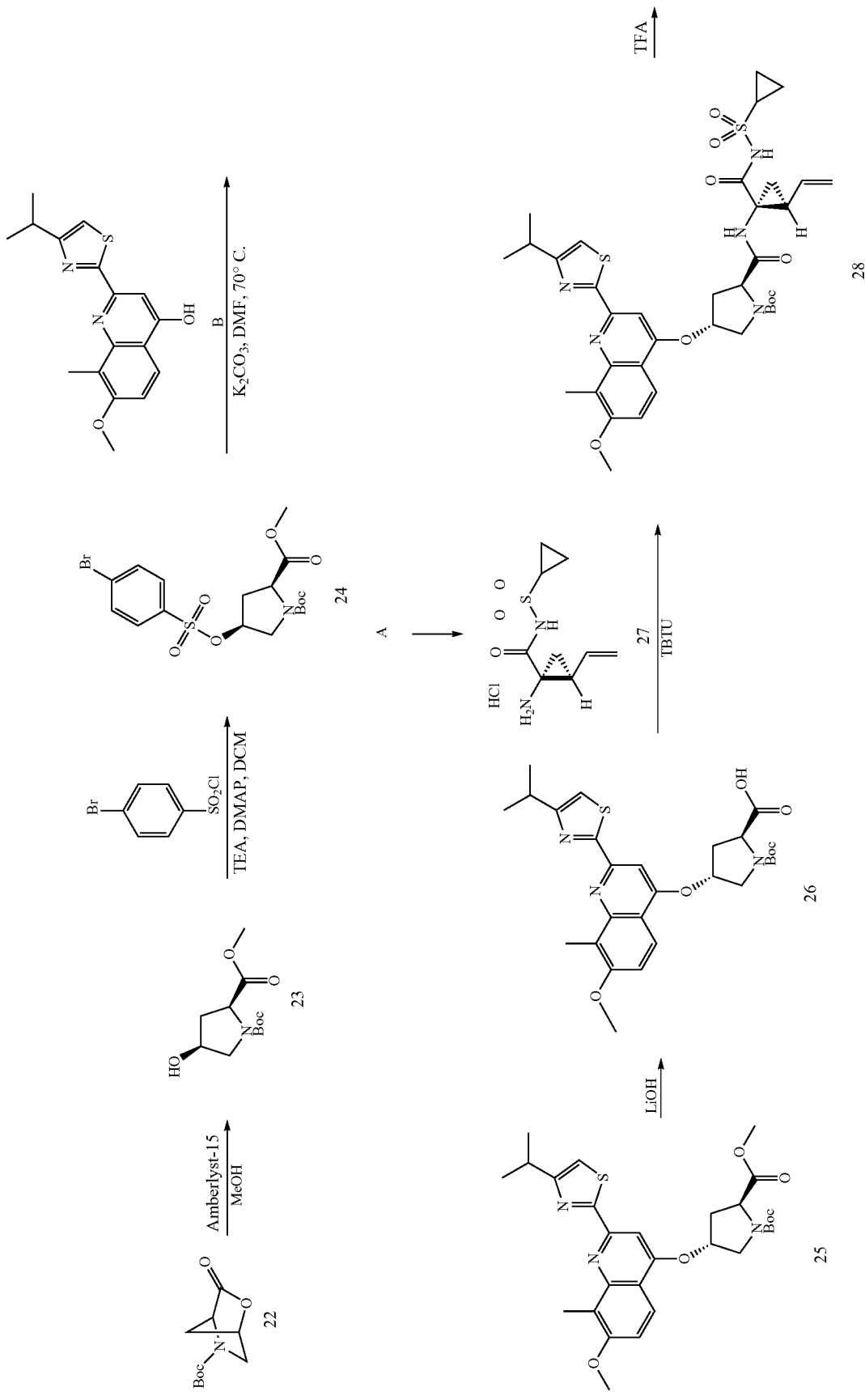

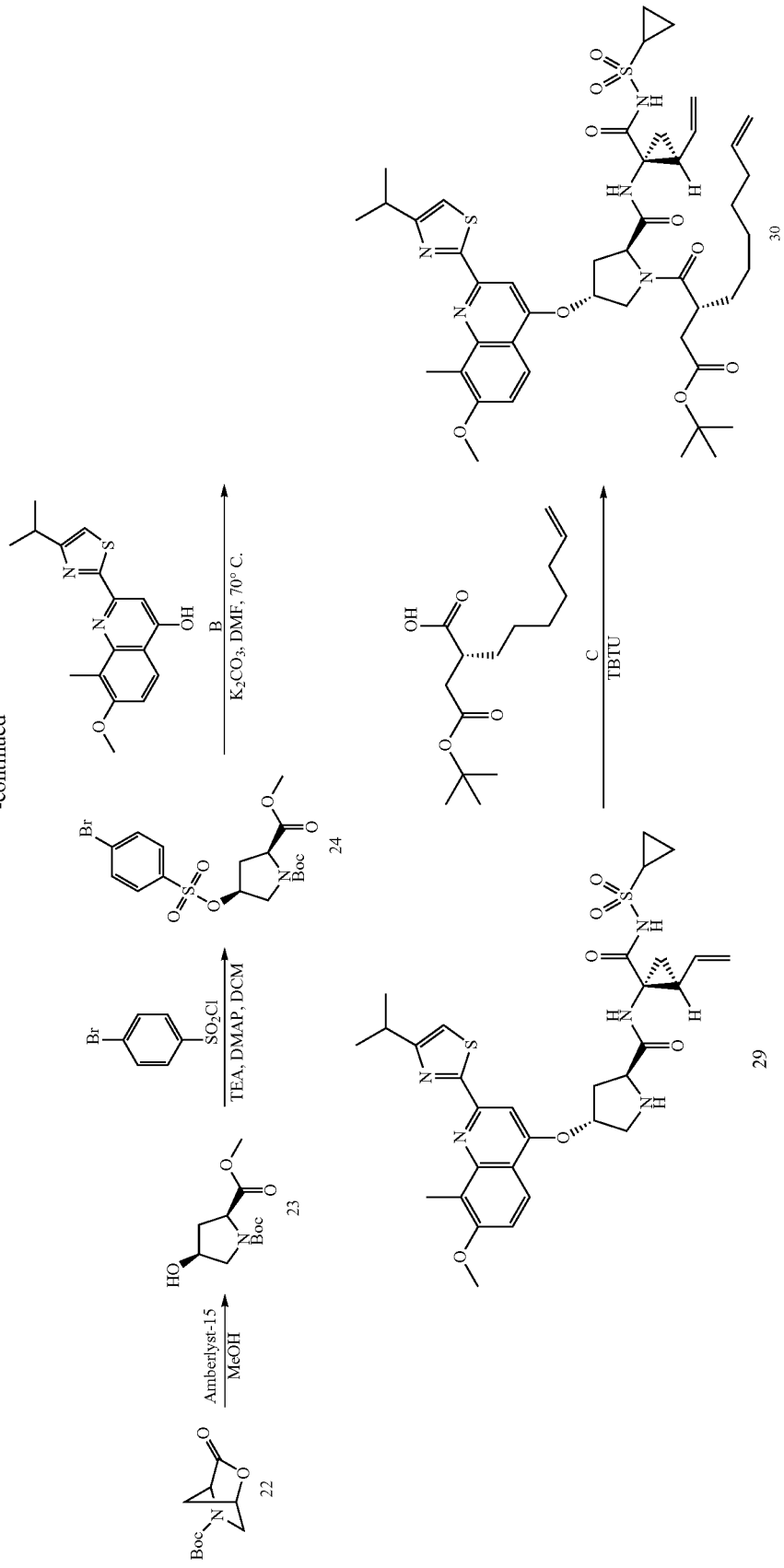

In accordance with Reaction Scheme D described above, the lactone (Compound 22, 1 equivalent) was stirred in methanol in the presence of Amberlyst-15® cation exchange resin (30% w/w) at room temperature for 18 hours. The resin was filtered and the filtrate evaporated to dryness to obtain cis-hydroxy proline methyl ester (Compound 23) having a purity of greater than 97%.

A solution of cis-hydroxypro line methyl ester (Compound 23, 1 equivalent), triethylamine and catalytic dimethylaminopyridine in dichloromethane was cooled to about 5° C. Methane sulfonyl chloride (1.5 equivalents), was added and stirred for 4h. The solution was washed with 1M citric acid, water and brine. The organic layer was concentrated to obtain the brosylate (Compound 24) and used for the next step without any purification.

To a solution of the brosylate compound (Compound 24, 1 equivalent) and hydroxyquinoline (Intermediate Compound B, 0.95 equivalents) in DMF (dimethyl formamide) solvent is added potassium carbonate (1.3 equivalents) at room temperature. The reaction was stirred at 70° C. until the reaction was complete (about 18 hours) and added to 1M citric acid with vigorous stirring. The solid was isolated by filtration and dissolved in dichloromethane containing 5% methanol and filtered. The filtrate was concentrated and purified by chromatography over silica gel to give Compound 25 (purity >98%).

Compound 25 (1 equivalent) was dissolved in tetrahydrofuran and a solution of aqueous lithium hydroxide (1.5 equivalents) added at about 5° C. The reaction was stirred at room temperature until complete, about 3 h. The reaction mixture was concentrated and the residue slowly added to 1M citric acid with vigorous stirring. The solid precipitated was filtered and dried. The residue obtained was heated in heptane, cooled and filtered to obtain the acid (Compound 26, purity >97%). This solid was used in the next step without further purification.

To a cold (about 5° C.) solution of 4.5 N HCl in 1,4-dioxane was added Intermediate Compound A (1.5 equivalents relative to compound 26) and then stirred at room temperature until reaction was complete (about 3 hours). The reaction mixture was concentrated and the residue, Compound 27, was dissolved in dimethylformamide. To this solution was added the acid (Compound 26, 1 equivalent) and diisopropylethyl amine (1.5 equivalent) followed by TBTU (1.3 equivalents) at 5° C. The reaction mixture was stirred at room temperature until completion (about 18 hours). The reaction mixture was then added to a solution of 1M citric acid with vigorous stirring. The solid precipitated was isolated by filtration, dissolved in dichloromethane/5%-methanol, dried and concentrated. The residue obtained was heated in heptane, cooled and filtered to give Compound 28 (purity >96%).

A solution of compound 28 (1 equivalent) in dichloromethane was cooled to 5° C. and trifluoroacetic acid (TFA, 2.0 w/v) was added slowly. The reaction mixture was stirred at room temperature until complete, about 4 hours. All the volatiles were evaporated, residue dissolved in dichloromethane and evaporated again and the residue was dissolved in dimethylformamide. This solution was cooled to 5° C., diisopropypethyl amine (10 equivalents) and Compound C (1.4 equivalent) were added followed by TBTU (1.3 equivalents). The reaction mixture was stirred at room temperature until completion, about 18 hours. The reaction mixture was added to 1M citric acid and the solid isolate by filtration. The solid was dissolved in dichloromethane/5%-methanol washed with brine, dried and evaporated to dryness. The residue purified over silica gel and then crystallized from isopropyl alcohol to give Compound 30 (purity >98%).

Step 2. Synthesis of ACH-0142684

The synthesis of Sodium Salt of 2R,6R,14aR,16aS,Z)-N-(cyclopropylsulfonyl)-6-(2-(3,3-difluoropiperidin-l-yl)-2-oxoethyl)-2-(2-(4-isopropylthiazol-2-yl)-7-methoxy-8-methylquinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide:

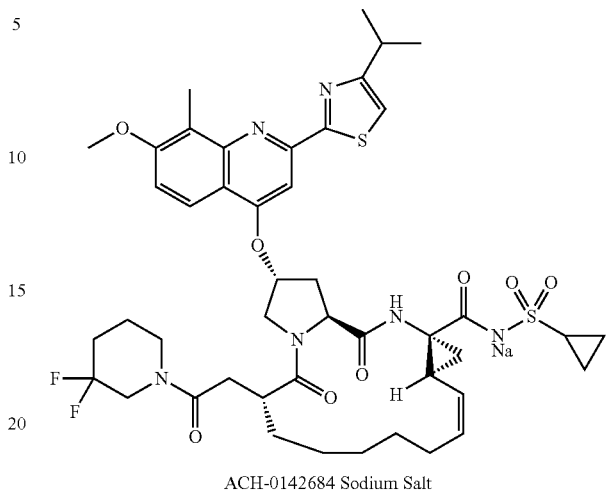

ACH-0142684 Sodium Salt

In accordance with Reaction Scheme E described above, Compound 30 (1 equivalent) was dissolved in toluene (1: 56 w/v) and the solution degassed by bubbling nitrogen for 15 minutes. The reaction temperature was raised to 80-110° C. and Hoveyda-Grubbs catalyst (1-2 mol %) as a solution in toluene was added. Heating was continued until completion of the reaction and cooled to room temperature. Toluene was evaporated and the residue was purified by chromatography over silica gel. Solvent was evaporated from pooled fractions and the residue stirred with heptane and the solid filtered to obtain compound 31 (purity >98%).

Compound 31 (1 equivalent) was dissolved in dichloromethane, cooled to 5° C. and trifluoroacetic acid (2-3 w/v) was added and stirred at room temperature for 4h. The reaction mixture was concentrated and the residue dissolved in dimethylfomamide and cooled to 5° C. before addition of diisopropylethyl amine (10 equivalents). TBTU (1.8 equivalents) was added followed by 3,3-difluoropiperidine hydrochloride (1.2 equivalents). The reaction was stirred until completion and added to 1M citric acid and solid collected by filtration. The solid was crystallized from ethylacetate/heptane to give ACH-0142684 (purity >98%). ACH-0142684 was suspended in methanol and aqueous sodium hydroxide (1.05 equivalents) was added at about 5° C. to give a clear solution. The reaction mixture was concentrated to dryness and the residue was stirred with IPA to give crystalline ACH-0142684.Na (Form G). The crystalline ACH-0142684.Na was dissolved in a mixture of methanol/ethyl acetate and the solution was added to pentane. The solid was collected by filtration and dried to give ACH-0142684.Na in the amorphous form (purity >98%).

Starting materials are generally readily available from commercial sources, such as Sigma-Aldrich Corp. (St. Louis, Mo.). It will be apparent that the final product and any intermediate(s) shown in the following schemes may be extracted, dried, filtered and/or concentrated, and may be further purified (e.g., by chromatography). Reaction Schemes, refers to any group consistent with the description of the compounds provided herein. An individual skilled in the art may find modifications of one or several of the synthetic steps described herein without diverting significantly from the overall synthetic scheme.

While the subject matter of this disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings without departing from the essential scope thereof. Therefore, it is intended that the disclosure not be limited to the particular disclosed embodiments but will include all embodiments falling within the scope of the appended claims.

What is claimed is:

1. The crystalline form of the sodium salt of ACH-1042684 comprising polymorph A.

2. The crystalline form of the sodium salt of ACH-1042684 of claim 1 wherein
polymorph A exhibits an X-ray powder diffraction pattern having the characteristic 2θ values of FIG. 8.

3. The crystalline form of the sodium salt of ACH-0142684 of claim 1, wherein polymorph A is characterized by an X-ray powder diffraction pattern obtained from a Cu Kα source which comprises peaks at 2θ values of 6.4, 16.3, 18.8, 21.8, and 23.7 +/−0.2; or 10.1, 17.4, 20.5, 21.6, 23.0, and 24.5 +/−0.2; or 11.6, 18.3, 21.6, 23.0, and 25.4 +/−0.2.

4. The crystalline form of the sodium salt of ACH-0142684 of claim 1, wherein polymorph A has a primary endotherm at 231.4° C. as determined by DSC.

5. The crystalline form of the sodium salt of ACH-0142684 of claim 1, wherein polymorph A has a Raman spectrum with the characteristic values of FIG. 7.

6. The crystalline form of the sodium salt of ACH 1042684 comprising polymorph B.

7. The crystalline form of the sodium salt of ACH-0142684 of claim 6, wherein polymorph B exhibits an X-ray powder diffraction pattern having the characteristic 2θ values of FIG. 12.

8. The crystalline form of the sodium salt of ACH-0142684 of claim 6, wherein polymorph B is characterized by an X-ray powder diffraction pattern obtained from a Cu Kα source which comprises peaks at 2θ values of 5.6, 6.8, 10.3, and 12.2 +/−0.2.

9. The crystalline form of the sodium salt of ACH-0142684 of claim 6, wherein polymorph B has a primary endotherm at 252° C. as determined by DSC.

10. The crystalline form of the sodium salt of ACH-0142684 of claim 6, wherein polymorph B has a Raman spectrum with the characteristic values of FIG. 11.

11. The crystalline form of the sodium salt of ACH 1042684 comprising polymorph C.

12. The crystalline form of the sodium salt of ACH-0142684 of claim 11, wherein polymorph C exhibits an X-ray powder diffraction pattern having the characteristic 2θ values of FIG. 15.

13. The crystalline form of the sodium salt of ACH-0142684 of claim 11, wherein polymorph C is characterized by an X-ray powder diffraction pattern obtained from a Cu Kα source which comprises peaks at 2θ values of 6.0, 11.6, 15.9, 18.6, and 21.3 +/−0.2; or 7.2, 12.1, 17.3, and 20.2 +/−0.2.

14. The crystalline form of the sodium salt of ACH-0142684 of claim 11, wherein polymorph C has a primary endotherm at 82.6° C. as determined by DSC.

15. The crystalline form of the sodium salt of ACH 1042684 comprising polymorph G.

16. The crystalline form of the sodium salt of ACH-0142684 of claim 15, wherein polymorph G exhibits an X-ray powder diffraction pattern having the characteristic 2θ values of FIG. 27.

17. The crystalline form of theسodium salt of ACH-0142684 of claim 15, wherein polymorph G is characterized by an X-ray powder diffraction pattern obtained from a Cu Kα source which comprises peaks at 2θ values of
5. 0, 9.5, 13.4, 15.0, 19.2, 20.9, and 22.5 +/−0.2; or
5.5, 9.8, 14.2, 15.7, 19.9, and 21.4 +/−0.2; or
7.8, 10.9, 14.7, 18.4, 20.6, and 22.0 +/−0.2.

18. The crystalline form of the sodium salt of ACH-0142684 of claim 15, wherein polymorph G has a primary endotherm at 284.3° C. as determined by DSC.

19. A composition comprising a crystalline sodium salt of ACH-0142684, wherein at least 90% of the crystalline sodium salt of ACH-0142684 is
the Form A polymorph, the Form B polymorph, the Form C polymorph, the Form D polymorph, the Form E polymorph, the Form F polymorph, the Form G polymorph, the Form H polymorph, the Form I polymorph, or a combination thereof.

20. A pharmaceutical composition comprising the crystalline sodium salt of ACH-0142684 according to claim 19, in combination with a physiologically acceptable carrier or excipient.

* * * * *